(12) United States Patent
Kim et al.

(10) Patent No.: US 7,101,844 B2
(45) Date of Patent: Sep. 5, 2006

(54) CYTOPLASMIC TRANSDUCTION PEPTIDES AND USES THEREOF

(75) Inventors: Dae-You Kim, Daejon Metropolitan (KR); Hae-Keun Oh, Daejeon Metropolitan (KR); Chang-Hyun Kim, Daejeon Metropolitan (KR); Jung-Hwan Kim, Daejeon Metropolitan (KR); Choon-Ju Jeon, Daejeon Metropolitan (KR); Ki-Tae Kim, Daejeon Metropolitan (KR); Yong-Soo Bae, Daejeon Metropolitan (KR); In-Soo Choi, Sewon-shi (KR)

(73) Assignee: Creagene, Inc., Daejeon Metropolitan (KR)

( * ) Notice: Subject to any disclaimer, the term of this patent is extended or adjusted under 35 U.S.C. 154(b) by 0 days.

(21) Appl. No.: 10/509,620

(22) PCT Filed: Mar. 28, 2003

(86) PCT No.: PCT/KR03/00630

§ 371 (c)(1),
(2), (4) Date: Sep. 29, 2004

(87) PCT Pub. No.: WO03/097671

PCT Pub. Date: Nov. 27, 2003

(65) Prior Publication Data

US 2005/0154188 A1    Jul. 14, 2005

(30) Foreign Application Priority Data

Mar. 29, 2002 (KR) ................... 10-2002-0017546

(51) Int. Cl.
*A01N 37/18* (2006.01)
(52) U.S. Cl. ........................................................ 514/2
(58) Field of Classification Search ............... None
See application file for complete search history.

(56) References Cited

U.S. PATENT DOCUMENTS

| 5,807,746 A | 9/1998 | Lin et al. |
| 6,043,339 A | 3/2000 | Lin et al. |

FOREIGN PATENT DOCUMENTS

| WO | 95/28494 | 10/1995 |
| WO | 95/34665 | 12/1995 |
| WO | 00/34308 | 6/2000 |

OTHER PUBLICATIONS

Wouters-Tyrou, et al., (J. Biol. Chem. 1991, 266, 17388-95.*
Wender et al; "The Design, Synthesis, and Evaluation of Molecules that Enable or Enhance Cellular Uptake: Peptoid Molecular Transporters"; ;PNAS, Nov. 2000, vol. 97, No. 24, pp. 13003-13008.
Schwarze et al; "In Vivo Protein Transduction: Delivery of a Biologically Active Protein into the Mouse"; Science, vol. 285, Sep. 3, 1999, pp. 1569-1572.
Ho et al; "Synthetic Protein Transduction Domains: Enhanced Transduction Potential in Vitro and in Vivo"; Cancer Research 61, Jan. 15, 2001, pp. 474-477.
Ford et al; "Protein Transduction: an Alterative to Genetic Invention?"; Gene Ther., Jan. 2001, vol. 8, No. 1, pp. 1-4.
Vocero-Akbani et al; "Transduction of Full-Length Tat Fusion Proteins Directly into Mammalian Cells: Analysis of T Cell Receptor Activation-Induced Cell Death"; Methods Enzymol., 2000, vol. 322, pp. 508-521.

* cited by examiner

*Primary Examiner*—Bruce R. Campell
*Assistant Examiner*—Satyanarayana R. Gudibande
(74) *Attorney, Agent, or Firm*—Nixon & Vanderhye P.C.

(57) ABSTRACT

The present invention relates to a cytoplasmic transduction peptide (CTP) showing transduction potential, as well as cytoplasmic remaining potential and various uses thereof. The CTP of this invention exhibits a transduction potential identical or higher than the conventional protein transduction, PTD, and a strong tendency to remain in the cytoplasm, so that it is very useful in inducing cytotoxic T lymphocytes (CTL) and a drug delivery system (DDS) targeting cytoplasm.

7 Claims, 17 Drawing Sheets

TAT (1x)
YGRKKRRQRRR

PTD-5 (8x)
YARAARRAARR

PTD

CTP512

PTD                    CTP512

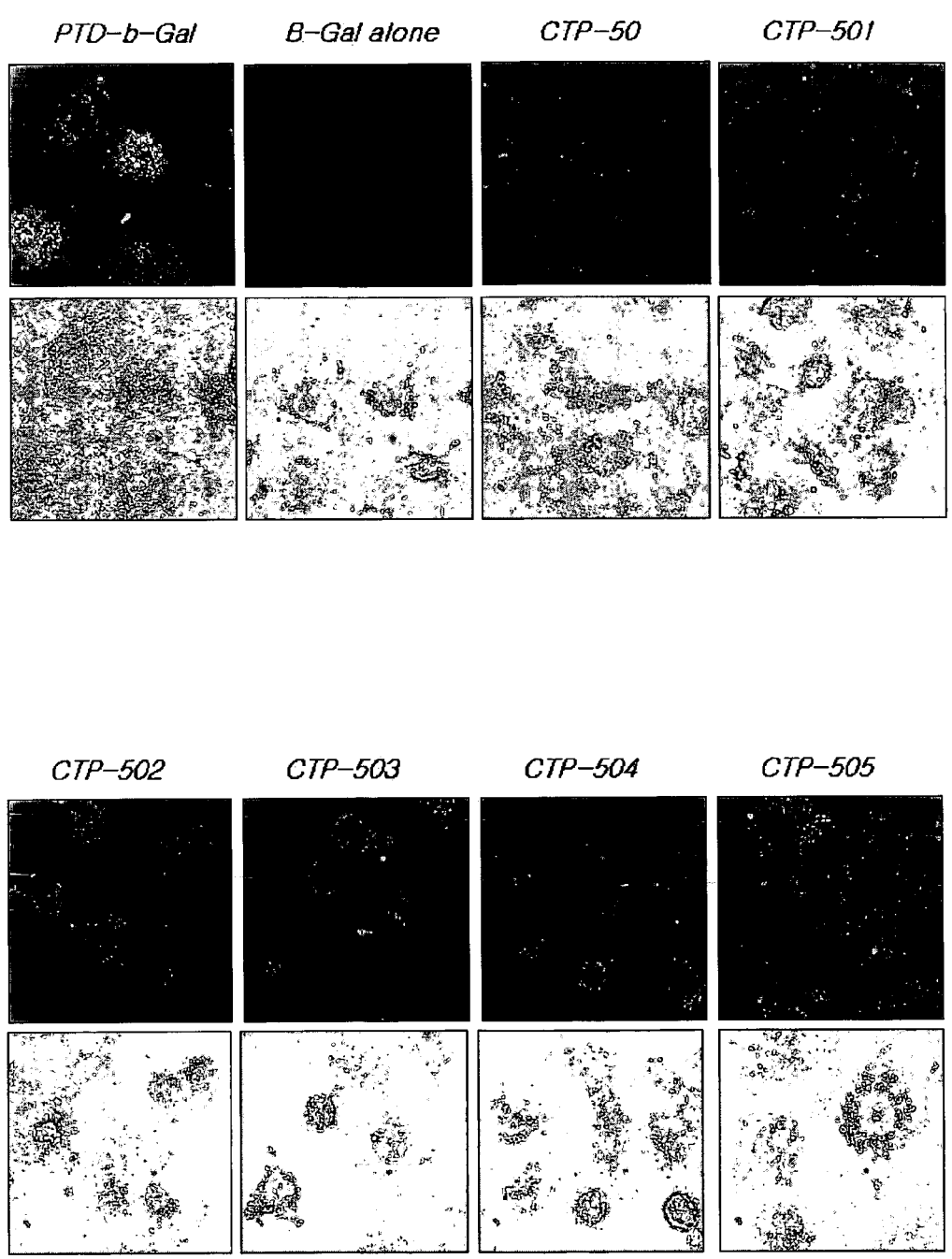

SEQUENCE LISTING

```
<160> NUMBER OF SEQ ID NOS: 15

<210> SEQ ID NO 1
<211> LENGTH: 11
<212> TYPE: PRT
<213> ORGANISM: Artificial Sequence
<220> FEATURE:
<223> OTHER INFORMATION: cytoplasmic transduction peptide

<400> SEQUENCE: 1

Tyr Gly Arg Arg Ala Arg Arg Arg Arg Arg Arg
 1               5                   10

<210> SEQ ID NO 2
<211> LENGTH: 11
<212> TYPE: PRT
<213> ORGANISM: Artificial Sequence
<220> FEATURE:
<223> OTHER INFORMATION: cytoplasmic transduction peptide

<400> SEQUENCE: 2

Tyr Gly Arg Arg Ala Arg Arg Ala Arg Arg
 1               5                   10

<210> SEQ ID NO 3
<211> LENGTH: 11
<212> TYPE: PRT
<213> ORGANISM: Artificial Sequence
<220> FEATURE:
<223> OTHER INFORMATION: cytoplasmic transduction peptide

<400> SEQUENCE: 3

Tyr Gly Arg Arg Ala Arg Arg Ala Ala Arg Arg
 1               5                   10
```

```
<210> SEQ ID NO 4
<211> LENGTH: 11
<212> TYPE: PRT
<213> ORGANISM: Artificial Sequence
<220> FEATURE:
<223> OTHER INFORMATION: cytoplasmic transduction peptide

<400> SEQUENCE: 4

Tyr Lys Arg Lys Ala Arg Arg Ala Ala Arg Arg
 1               5                  10

<210> SEQ ID NO 5
<211> LENGTH: 11
<212> TYPE: PRT
<213> ORGANISM: Artificial Sequence
<220> FEATURE:
<223> OTHER INFORMATION: cytoplasmic transduction peptide

<400> SEQUENCE: 5

Tyr Ala Arg Lys Ala Arg Arg Ala Ala Arg Arg
 1               5                  10

<210> SEQ ID NO 6
<211> LENGTH: 11
<212> TYPE: PRT
<213> ORGANISM: Artificial Sequence
<220> FEATURE:
<223> OTHER INFORMATION: cytoplasmic transduction peptide

<400> SEQUENCE: 6

Tyr Lys Arg Ala Ala Arg Arg Ala Ala Arg Arg
 1               5                  10

<210> SEQ ID NO 7
<211> LENGTH: 11
<212> TYPE: PRT
<213> ORGANISM: Artificial Sequence
<220> FEATURE:
<223> OTHER INFORMATION: cytoplasmic transduction peptide

<400> SEQUENCE: 7

Tyr Glu Arg Glu Ala Arg Arg Ala Ala Arg Arg
 1               5                  10

<210> SEQ ID NO 8
<211> LENGTH: 11
<212> TYPE: PRT
<213> ORGANISM: Artificial Sequence
<220> FEATURE:
<223> OTHER INFORMATION: cytoplasmic transduction peptide

<400> SEQUENCE: 8

Tyr Ala Arg Glu Ala Arg Arg Ala Ala Arg Arg
 1               5                  10

<210> SEQ ID NO 9
<211> LENGTH: 11
<212> TYPE: PRT
<213> ORGANISM: Artificial Sequence
<220> FEATURE:
<223> OTHER INFORMATION: cytoplasmic transduction peptide

<400> SEQUENCE: 9

Tyr Gly Arg Ala Ala Arg Arg Ala Ala Arg Arg
 1               5                  10
```

```
<210> SEQ ID NO 10
<211> LENGTH: 11
<212> TYPE: PRT
<213> ORGANISM: Artificial Sequence
<220> FEATURE:
<223> OTHER INFORMATION: cytoplasmic transduction peptide

<400> SEQUENCE: 10

Tyr Arg Arg Ala Ala Arg Arg Ala Ala Arg Ala
 1               5                  10

<210> SEQ ID NO 11
<211> LENGTH: 11
<212> TYPE: PRT
<213> ORGANISM: Artificial Sequence
<220> FEATURE:
<223> OTHER INFORMATION: cytoplasmic transduction peptide

<400> SEQUENCE: 11

Tyr Pro Arg Ala Ala Arg Arg Ala Ala Arg Arg
 1               5                  10

<210> SEQ ID NO 12
<211> LENGTH: 11
<212> TYPE: PRT
<213> ORGANISM: Artificial Sequence
<220> FEATURE:
<223> OTHER INFORMATION: cytoplasmic transduction peptide

<400> SEQUENCE: 12

Pro Ala Arg Ala Ala Arg Arg Ala Ala Arg Arg
 1               5                  10

<210> SEQ ID NO 13
<211> LENGTH: 11
<212> TYPE: PRT
<213> ORGANISM: Artificial Sequence
<220> FEATURE:
<223> OTHER INFORMATION: cytoplasmic transduction peptide

<400> SEQUENCE: 13

Tyr Gly Arg Arg Arg Arg Arg Arg Arg Arg Arg
 1               5                  10

<210> SEQ ID NO 14
<211> LENGTH: 11
<212> TYPE: PRT
<213> ORGANISM: Artificial Sequence
<220> FEATURE:
<223> OTHER INFORMATION: cytoplasmic transduction peptide

<400> SEQUENCE: 14

Tyr Arg Arg Arg Arg Arg Arg Arg Arg Arg Arg
 1               5                  10

<210> SEQ ID NO 15
<211> LENGTH: 11
<212> TYPE: PRT
<213> ORGANISM: Human immunodeficiency virus type 1

<400> SEQUENCE: 15

Tyr Gly Arg Lys Lys Arg Arg Gln Arg Arg Arg
 1               5                  10
```

US 7,101,844 B2

CYTOPLASMIC TRANSDUCTION PEPTIDES AND USES THEREOF

This application is the US national phase of international application PCT/KR03/00630 filed 28 Mar. 2003, which designated the US and claims benefit of KR Application No. 10-2002-0017546 filed 29 Mar. 2002, the entire contents of each of which are incorporated herein by reference.

FIELD OF THE INVENTION

The present invention relates to a cytoplasmic transduction peptide (CTP), particularly to a cytoplasmic transduction peptide showing transduction potential as well as a cytoplasmic localization potential and the various uses thereof.

DESCRIPTION OF THE RELATED ART

In 1998, Tat protein of HIV-1 in a cell medium was revealed to actively transduce into cells (Green and Loewenstein, 1988; and Frankel and Pabo, 1988), and since then the mechanism regulating protein transduction into cells has been intensively researched. As a result, it has been elucidated that a protein transduction domain (PTD) consisting of 9 basic amino acids (RKKRRQRRR) in Tat protein plays a pivotal role in crossing cell membranes (Vives et. al., 1997; Futaki et. al., 2001; Suzuki et. al., 2002; Hakansson et. al., 2001; Tyagi et. al., 2001; Rusnati et. al., 1997).

The fact that Tat PTD (RKKRRQRRR) is mainly constituted of amino acids with positive charges, has triggered research to analyze the transduction efficiency of PTD with substituted amino acid sequences. This research has shown that the Arg polycationic homopolymer (RRRRRRRRR) exhibits a 20-fold transduction efficiency greater than Tat PTD (Wender et. al., 2000). In the case of substitution with Lys, Orn or His other than Arg, no higher transduction efficiency than that of Tat PTD has been found. In addition, the citrulline polymer deprived of positive charges in the guanidine groups of the Arg residues has shown negligible transduction potential (Michelle et. al., 2000). These findings make it possible to reason that the basic amino acids in PTD, inter alia, the guanidine groups of Arg, serve as pivotal factors in transduction.

It has been suggested that the fusion protein prepared by attaching PTD to other peptides or proteins effectively transports into cells. Based on this finding, various attempts have been made to develop novel applications of PTD (Schwarze et. al., 1999; Kim et. al., 1997; Schwarze et. al., 2000; Gius et. al., 1999; Nagahara et. al., 1998; Mai et. al., 2001; Xia et. al., 2001; Embury et. al., 2001; Rothbard et. al., 2000; Lewin et. al., 2000 and Vocero-Akbani et. al., 1999). Most attempts have been focused on the delivery of proteins, nucleic acids and drugs into cells using the PTD of Tat protein.

Besides Tat protein, the Antp protein of *Drosophila melanogaster* and the VP22 protein of HSV have been reported as having a transduction domain (Derossi et. al., 1994; Derossi et. al., 1996; Derossi et. al., 1998; Joliot et. al., 1991; and Elliott et. al., 1997); however, their PTD structure and mechanism for transduction remain unclear.

The amino acid sequences of the PTDs from Tat, Antp and VP22 commonly show basic amino acid-richness but their sequence homology has not been discovered. HIV-1 Tat shows a random coil structure in NMR and CD spectrum analysis; however, the tendency toward an α-helix structure emerges strongly in a protein structure predictive program (Loret et. al., 1991; Gregoire et. al., 1996; Mujeeb et. al., 1994; and Ho et. al., 2001). However, the most manifest difference in peptides having membrane transduction potential so far known lies in the size limit of their fusion partners. Antp is capable of carrying proteins of fewer than 100 amino acids in length and Tat, while VP22 is able to carry proteins of more than 1,000 amino acids in length (Schwarze et. al., 2000; Fawell et. al., 1994; and Schwarze et. al., 1999).

Although showing other characteristics than PTD, a signal sequence [known as membrane transduction sequence (MTS) or cytoplasmic penetration peptide (CPP)] in FGF (Fibroblast Growth Factor) has been reported as having membrane transduction potential (Hawiger J. 1999; Hawiger J. 1997; Lin et. al., 1995; Liu et. al., 1996; Rojas et. al., 1998; and Wang et. al., 2002). The signal sequence is able to easily transduce across cell membranes but unable to transduce into the nucleus due to the lack of a nuclear localization sequence (NLS). Most MTS molecules in cells ultimately enter into the endoplasmic reticulum because of the property of the signal sequence itself, and its transportation potential to macromolecules such as β-galactosidases, shows only 30% of that of PTD.

DETAILED DESCRIPTION OF THIS INVENTION

The present inventors have made intensive research to develop a series of novel peptides exhibiting excellent transduction potential as well as a strong tendency to remain in the cytoplasm after transduction, without migrating into the nucleus. As a result of finding a peptide with a unique amino acid composition which shows the desired characteristics, therefore the present invention has been accomplished. In addition, the present inventors have completed a cytoplasmic transduction system comprising a cytoplasmic transduction of biologically active molecules conjugated to the peptide. Furthermore, using the cytoplasmic transduction system described above, the present inventors have accomplished a method for delivering a biologically active molecule, such as a protein to a specific organ or tissue.

Accordingly, one object of this invention is to provide a cytoplasmic transduction peptide.

Another object of this invention is to provide a nucleic acid molecule encoding the cytoplasmic transduction peptide.

Still another object of this invention is to provide a cytoplasmic transduction system.

A further object of this invention is to provide a method for delivering a biologically active molecule into a cytoplasm.

Other objects and advantages of the present invention will become apparent from the detailed description which follows taken in conjunction with the appended claims.

One aspect of this invention is a cytoplasmic transduction peptide characterized by a genuine cell membrane transduction potential. Here, when a cell is treated with the cytoplasmic transduction peptide for a period of time, then treated with a protease, a cell membrane transduction caused by the cytoplasmic transduction peptide continues to occur; and after the cell membrane transduction, the cytoplasmic transduction remains in the cytoplasm.

The PTDs known so far essentially comprise a nuclear localization sequence (NLS) which imports proteins into the nucleus. To date, 91 NLSs have been revealed, most of which contain a high frequency of basic amino acids, although they are not homologous in their amino acid sequences (Cokol et. al., 2000). However, it has been reported that some NLSs contain many glycine residues instead of basic amino acids (Bonifaci et al., 1997). Certain motifs can be assigned a NLS, according to the following two criteria. First, when suspected NLS motif is removed, nuclear transport does not occur; secondly, when the motif is fused to a non-nuclear protein, transport of the fusion protein into the nucleus occurs. The motif which meets the two criteria is called a NLS (Tinland et al., 1992; Moede et al., 1999). To prevent the transport of a PTD fusion protein into the nucleus, the motif can readily be anticipated to remove the NLS from the PTD. However, it is common for the NLS per se to play a pivotal role in PTD function. Therefore, it is practically difficult to design and construct a cytoplasmic transduction peptide for transporting fusion protein into only the cytoplasm, but not into the nucleus.

NLS is a region bound to importin-α protein, allowing nuclear proteins to enter into the nucleus. In addition, non-nuclear proteins fused to a NLS can be transported into the nucleus. In HIV-1 Tat protein, there is no clear distinction between the PTD and the NLS, and some of their sequences overlap to a TAR binding region of Tat in HIV-1 transcription. Actually PTD (YGRKKRRQRRR) contains the nuclear localization signal (GRKKRR) of the HIV-1 Tat protein. The interaction between the NLS and the nuclear transport factor, importin-α, permits PTD to be introduced into the nucleus.

For example, antigens transported into cytoplasm will be processed by proteasomes, and then presented on the cell surface by MHC class I molecules. However, when PTD is used as an antigen carrier, PTD-conjugated antigens will be moved into the nucleus after membrane transduction, due to the NLS of the PTD, so that the PTD-antigen in the nucleus may not be presented efficiently by MHC class I molecules. In addition, the mobility of the PTD into the nucleus is not helpful in delivering proteins or therapeutic drugs, which targets molecules in the cytoplasm. To overcome such a shortcoming, it is necessary that a cytoplasmic transduction peptide, CTP, showing not only excellent membrane transduction potential, but also a strong tendency to remain in cytoplasm after transduction without migrating into nucleus, be developed by removing the NLS function from the PTD.

To develop CTP, the present inventors have studied the relationship between the function and structure of PTD by means of the molecular modeling approach, and as a result, have designed and constructed a PTD variant, i.e. CTP, in which the NLS function of PTD binding to importin-α protein is removed by enhancing, rather than reducing, the membrane transduction efficiency.

The new term used first herein, "cytoplasmic transduction peptide (CTP)", refers to a peptide showing not only an efficient transduction potential but also a strong tendency to remain in the cytoplasm without migrating into the nucleus after transduction. Such a novel CTP was first and originally developed by the present inventors. In the interim, the conventional PTDs have been challenged with respect to the authenticity of their transduction potential (43–46). The CTP of the present invention is a genuine transduction peptide, completely overcoming the limitations of PTD in the application of its transduction property previously raised in the art.

In the CTP of this invention, the peptide length may vary within the acceptable scope of the art, preferably 9–20 amino acids, more preferably 9–15 amino acids, and most preferably, to about 11 amino acids.

Since the CTP of this invention is a genuine transduction peptide, where cells are treated with CTP for an appropriate time, and then treated with proteases (e.g. trypsin, chymotrypsin or subtilisin), the transduction phenomenon continues to occur. As demonstrated in the Examples section below, where the conventional PTDs, in particular the Tat-derived PTD applied to cells are treated with protease, the transduction yield is markedly decreased. Such a disappearance of transduction can be explained in the following way: The rapid transduction potential of the PTD reported previously could be due to the artificial infiltration of the membrane-attached PTD during the cell fixation procedure, rather than the authentic membrane permeability of the PTD peptide, because the PTD peptide itself has a high affinity for the cell membrane via electrostatic interaction between the positive charges of the PTD and the negative charges of the cell membrane.

The principle strategy of this invention is that amino acid residues exhibiting α-helix stabilization or α-helix formation-enhancing properties as well as having positive-charged R-group are incorporated into the peptide, so that its binding affinity to importin-α is minimized and its transduction potential is improved or at least maintained.

The term "α-helix formation-enhancing amino acid" used herein refers to an amino acid having a strong tendency to form or stabilize α-helix conformation. The description of such a tendency has been disclosed in W. H. Freeman's *Proteins: Structure and Molecular Properties*, p. 235 (1983). According to its preferred embodiment, the α-helix formation-enhancing amino acid essentially comprised in the peptide of this invention includes alanine, arginine and lysine; more preferably arginine and lysine; and most preferably, arginine.

The term "amino acid having a positive-charged R-group" used herein refers to a basic amino acid, such as arginine, lysine and histidine, preferably arginine and lysine, and most preferably, arginine.

According to its preferred embodiment, the CTP of this invention comprises α-helix formation-enhancing amino acids having a positive-charged R-group as a pivotal amino acid. The term "a pivotal amino acid" refers to α-helix formation-enhancing amino acids having a positive-charged R-group essentially comprise the peptide of this invention, thereby producing the desired function of the peptide. Therefore, at least 3, preferably at least 5, more preferably at least 7, and most preferably at least 8 of the pivotal amino acids comprise the present peptide.

According to the preferred embodiment, the peptide of this invention forms an α-helical structure and comprises at the site of its N-terminal, an amino acid residue which has a relatively high freedom at the $\phi$ and $\psi$ rotations of the peptide unit. With respect to the rotations, "$\phi$" refers to the rotation about the Cα-N single bond and "$\psi$" refers to rotation about Cα-C single bond. The amino acid residue which has a relatively high freedom at the $\phi$ and $\psi$ rotations is glycine or alanine, or most preferably, glycine.

According to a specific example of this invention, the CTP of this invention comprises at least a peptide represented by the following formula: A-$X_1$-$X_2$-B-$X_3$-$X_4$-$X_5$-$X_6$-$X_7$-$X_8$. In this formula, A is an amino acid exhibiting relatively high freedom at the $\phi$ and $\psi$ rotations of the peptide unit, and at least 3 of the residues of $X_1$, $X_2$, B, $X_3$, $X_4$, $X_5$, $X_6$, $X_7$, and $X_8$ are arginine or lysine.

According to the preferred embodiment, A is glycine or alanine, or more preferably, A is glycine.

Preferably, at least 4, more preferably at least 5, still more preferably at least 6, and most preferably at least 7 of the residues of $X_1$, $X_2$, B, $X_3$, $X_4$, $X_5$, $X_6$, $X_7$, and $X_8$ are arginine or lysine, or preferably, arginine.

According to a specific example of this invention, the CTP of this invention comprises an amino acid sequence selected from the group consisting of SEQ ID NOs:1–14. Preferably, the peptide of this invention comprises an amino acid sequence selected from the group consisting of SEQ ID NOs:1–6, 8–10 and 13–14. More preferably, the peptide of this invention comprises an amino acid sequence selected from the group consisting of SEQ ID NOs:1–2 and 13–14. Still more preferably, the peptide of this invention comprises an amino acid sequence selected from the group consisting of SEQ ID NOs:1 and 13. Most preferably, the peptide of this invention comprises an amino acid sequence of SEQ ID NO:1.

The peptides of this invention may be prepared by selecting the natural-occurring peptides and by synthesizing peptides having the characteristics described above (e.g., synthesis by use of a peptide synthesizer, Applied Biosystems Model 433). In addition, the peptides of this invention may be prepared by modifying (mutating) a natural-occurring protein transduction domain.

Therefore, in another aspect of this invention, a cytoplasmic transduction peptide is prepared by substituting at least one amino acid in the protein transduction domain (PDD) of Tat protein with an α-helix formation-enhancing amino acid.

PTD has a wide variety of origins, typically an HIV-1 Tat protein. The example of the amino acid sequence of PTD is set forth in SEQ ID NO:15.

According to the preferred embodiment, the α-helix formation-enhancing amino acid includes alanine and arginine, but more preferably arginine.

According to a specific example of this invention, the cytoplasmic transduction peptide of this invention comprises an amino acid sequence selected from the group consisting of SEQ ID NOs:1–2 and 13–14. More preferably, the peptide of this invention comprises an amino acid sequence selected from the group consisting of SEQ ID NOs:1 and 13. Most preferably, the peptide of this invention comprises an amino acid sequence of SEQ ID NO:1.

Unlike the conventional PTDs transported into the cell during cell fixation, the CTP of this invention is a genuine transduction peptide and exhibits improved transduction potential, as well as a strong tendency to remain in the cytoplasm without migrating into the nucleus, as are demonstrated in the Examples section hereunder. Consequently, the applicability of this CTP is very high.

In still another aspect of this invention, a nucleic acid molecule encoding the CTP of this invention is provided. The nucleic acid is a single stranded or double stranded deoxyribonucleotide or ribonucleotide, and may include known analogues of natural-occurring nucleotides. The nucleic acid may be carried in a vector.

In a further aspect of this invention, a cytoplasmic transduction system comprising the CTP of this invention and a biologically active molecule covalently linked to CTP is provided.

The biologically active molecule linked to CTP is a substance manifesting a biological effect by acting on a biomolecule existing in the cytoplasm. For example, it includes proteins or peptides such as regulation factors, enzymes and antibodies, chemical substances such as drug, carbohydrates, lipids, glycolipids and nucleotide sequences, such as DNA (cDNA or gDNA) and RNA (mRNA or antisense RNA), but not limited to these.

In the cytoplasmic transduction system of this invention, the molecules covalently linked to the CTP may be attached to the N-terminal or C-terminal of the CTP. The covalent bonds may be formed according to the conventional methods known in the art, depending on the type of biologically active molecules present. For example, when using a protein as a biologically active molecule, recombinant technologies may be used to generate a fusion gene encoding CTP-protein conjugate, and then, through cloning and its expression in cells, the CTP-protein is produced. The detailed descriptions of the genetic engineering technologies indicated herein is found in Joseph Sambrook, et al., *Molecular Cloning, A Laboratory Manual*, Cold Spring Harbor Laboratory Press, Cold Spring Harbor, N.Y.(2001).

In addition, the CTP-biologically active molecule conjugate may be prepared by the use of various crossing agents. The crossing agent used should not inhibit the transduction potential and the tendency of CTP to remain in the cytoplasm, or the activity of the biologically active molecule. For example, the crossing agent may include N-succinimidyl iodoacetate, N-Maleimidobutyryloxysuccinamide ester, 1,5-difluoro-2,4-dinitorbenzene, bisdiazobenzidine, 3,3'-dithio-bis-(sulfosuccinimidyl-propionate), ethylene glycol bis-(succinimidylsuccinate) and dicyclohexyl carbodiimide, but is not limited to these agents. For biologically active molecules which are inactive until the CTP is released, it is preferable that the crossing agent be cleavable in vivo. For example, crossing agents containing carboxylic acid esters and/or disulfide bonds are useful.

In addition, where CTP is linked to a virus vaccine vector (e.g., poliovirus vector), cells infected with the vector express a protein comprising the CTP. The protein is transported to the surrounding cells by virtue of the CTP and remains in the cytoplasm. Therefore, it would be anticipated that a novel vaccine vector would exhibit improved cytotoxic T lymphocyte (CTL) induction by means of the CTP.

In a still further aspect of this invention, a method for delivering a biologically active molecule into the cytoplasm of a cell is provided. It comprises bringing into contacting the cytoplasmic transduction system (i.e. a CTP-biologically active molecule conjugate) to cell or individual.

Where the cytoplasmic transduction system of this invention is directly applied to a cell, the present method permits to the delivery of a specific molecule into the cell and causes it to remain in the cytoplasm. (See the description in the Examples section hereunder.) The cells to which this invention is applicable may vary. For example, they may includes T cells, B cells, macrophages, dendritic cells, endothelial cells, eptithelial cells, keratinocytes, muscle cell, fibroblast, tumor cell, splenocyte, liver cell, kidney cells, cardiac tissue cells, lymphoidal cells and neurons. The conditions suitable for this invention vary, depending on the types of CTP, molecules delivered and cells to which they are applied. For example, where the molecule delivered has a high molecular weight, the treatment time with CTP-conjugate should be longer. Generally, the temperature for treatment ranges from about 22° C.–37° C., and the time period ranges from 10 min to 30 hr. Furthermore, where dendritic cells are pulsed with antigen conjugated to the CTP, a more potential dendritic cell vaccine can be obtained. Therefore, the present method is particularly suitable in inducing CTL-reactions. Among the transduction systems known so far, there are no systems capable of delivering a specific molecule into the cytoplasm not into the nucleus. The present system and method make it possible to deliver a specific molecule into the cytoplasm only.

Where the cytoplasmic transduction system of this invention is applied to an individual, it may be administered via a variety of routes. For example, intraperitoneal or intravenous injections can be carried out. As described in the Examples section, where the cytoplasmic transduction system of this invention is applied to an individual, it has a migration preference in vivo to a particular organ or tissue (liver or lymph node). Accordingly, the present method is advantageously suitable in delivering bioactive molecules to liver or lymph nodes. In addition, the cytoplasmic transduction system of this invention is very likely to migrate into a specific region in an organ. Among the transduction systems known so far, there is no system to deliver a specific molecule, inter alia, a macromolecule (e.g. β-galactosiase), when applied to an individual, not the cell. The present system and method make it possible to deliver a specific molecule when applied to an individual. Therefore, the present method is significantly valuable as a drug delivery system for chemical drugs and bio-drugs. Preferably, the term "individual" used herein means animals, more preferably, mammals, and most preferably, humans.

According to the present method, since the biologically active molecule delivered remains in the cytoplasm, the side effects associated with conventional PTDs that result from transport into the nucleus can be completely overcome.

To date, a wide variety of transduction systems have been developed. However, most of them transport molecules into the nucleus after passing through the cell membrane. It had been believed in the art that the targeting to a specific molecule in the cytoplasm was not possible yet. The present invention completely solves such a technical problem in the art. The characteristics of CTP, i.e. its transduction potential and tendency to remain in the cytoplasm, are very useful in various practical fields.

The following specific examples are intended to be illustrative of the invention, and should not be construed as limiting the scope of the invention as defined by the appended claims.

BRIEF DESCRIPTION OF THE DRAWINGS

FIG. 4b schematically shows the results of FIG. 4a.

FIG. 5a shows the subcellular localization of the PTD and CTP candidates of this invention.

In FIGS. 6a–6b, panels 1–16 represent PTD-β-gal, MTS-β-gal, CTP501-β-gal, CTP502-β-gal, CTP503-β-gal, CTP504-β-gal, CTP505-β-gal, CTP506-β-gal, CTP507-β-gal, CTP508-β-gal, CTP509-β-gal, CTP510-β-gal, CTP511-β-gal, CTP512-β-gal, CTP513-β-gal and CTP514-β-gal, respectively.

EXAMPLES

Example 1

The Process for Designing CTP

Figure 1:
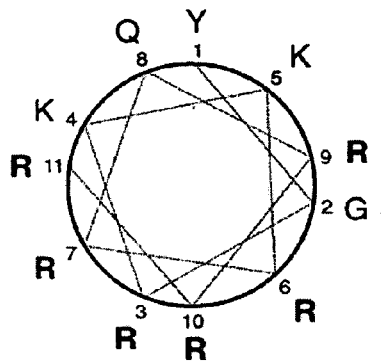
FIG. 1 shows the wheel plot of PTD and PTD-5 known in the art.
Figure 1:
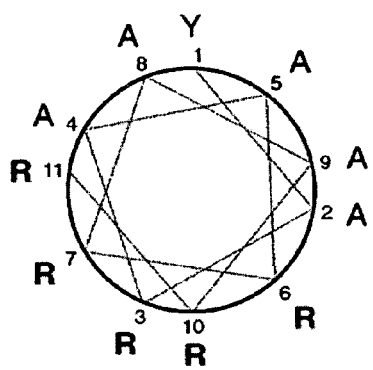

To construct the CTP of this invention, it was necessary that a membrane transduction peptide be deprived of its NLS function; therefore the present inventors researched the functional requirements of NLS. To understand the structural characteristics of NLS, the inventors studied the structure of mouse importin-α protein bound to the NLS region of the nuclear protein nucleoplasmin (Fontes et al., 2000). Lys residues of NLS are bound to the binding cleft of importin-α with highly distributed negative charges in extended and twisted conformations. The NLS of nucleoplasmin has 4 consecutive Lys residues in the region of the C-terminal, which show an extended conformation in the binding cleft of importin-α and form as many salt bridges as possible to the negative-charged binding cleft.

Therefore, although the binding structure between the importin-α protein and the Tat PTD has not yet been elucidated, it could be understood that the rigidity of the α-helical structure serves as an obstacle in the binding of the NLS region of the PTD to the importin-α. As suggested by NMR analysis, since the PTD of the HIV-1 Tat has an extended coil conformation rather than an α-helix, it is favorable in binding to importin-α.

A series of CTPs developed in accordance with the strategy of this invention were elucidated as having a strong tendency toward an α-helical conformation, as examined in the structural analysis by molecular modeling. Therefore, the present inventors have established a primary strategy for constructing a novel transduction peptide, in which the NLS region of the PTD that is expected to bind to importin-α is modified to show a much stronger tendency toward an α-helical conformation than a naturally occurring PTD. As a result, the tendency toward an extended coil conformation can also be minimized, the binding affinity to importin-α can be minimized and the transduction potential becomes identical to, or higher than, the native PTD as well.

Since, the binding cleft in importin-α to NLS has an extended and twisted conformation, it would be recognized that where the CTP of this invention has a stronger tendency toward an α-helix conformation, the binding between CTP and importin-α is significantly reduced due to the rigidity of α-helix conformation. Thus the CTP or the CTP-fused protein or the peptide can remain in the cytoplasm rather than transferring into the nucleus.

In the present invention, although CTPs have been developed with the adjustment of amino acid sequences by molecular modeling based on the PTD and its mutants, as prepared by the Dowdy Laboratory at Washington University School of Medicine, they are completely different from those of Dowdy's in several respects, inter alia, function. Dowdy's research results originated from transduction experiments with fluorescent-labeled peptides of 15 amino acid residues, most of which have shown to be transduced into the nucleus. However, the CTP derivatives of this invention have been selected from CTP candidates in the sense that a high molecular weighted protein such as β-galactosidase (M.W. 1,200,000) fused to CTP, is delivered into the cytoplasm rather than the nucleus.

Seven types of PTD reported by the Dowdy group were analyzed by molecular modeling, and it was revealed that all of them stably formed amphipathic α-helix conformations. While the mechanism governing the passage of an α-helix across a cell membrane remains unknown, the present inventors have concluded that the interactions between an α-helix and a cell membrane by dipole moment, and the electrosatic potential of the α-helix plays an important role in the transduction of PTD.

In addition, PTD derivatives showing the distribution of basic amino acids similar to PTD were fused to β-galactosidase, and then their transduction potential was measured. Inconsistent with previous reports, it was observed that PTD derivatives such as PTD5 fused to β-galactosidase show a decreased transduction efficiency of more than 50-fold compared to PTD (Tat), while the Dowdy group has reported that PTD5 delivers peptides into the cell with an 8-fold higher efficiency than PTD (TAT). On the basis of these results, the present inventors have reasoned that the transduction efficiency of peptides cannot reflect that of the fusion protein.

Meanwhile, although β-galactosidase fused to PTD5 shows a 50-fold lower transduction potential than its wild type PTD fusion protein, PTD5 exhibits a relatively increased pattern in terms of the extent it remains in the cytoplasm as compared to PTD. Therefore, the CTPs of this invention have been developed on the basis of this result.

As shown in FIG. 1, where PTD5 forms an α-helix, 5 Args (Arg5: Nos. 3, 6, 7, 10 and 11 Arg) are distributed on one face of the α-helix.

The principle strategy for developing CTPs is as follows: While maintaining 5 arginines (Arg5), amino acids 2 and 4 alanines around arginines 6 and 11 of an α-helix were substituted with positively charged arginine (CTP503, 507, 508 and 509), negatively charged glutamic acid (CTP505 and 506), glycine with small and free structural characters (CTP 504), or proline with a restricted structure (CTP 501 and 502), and then the sequences of the CTP candidate peptides were analyzed. (See Table 1.)

Figure 2:
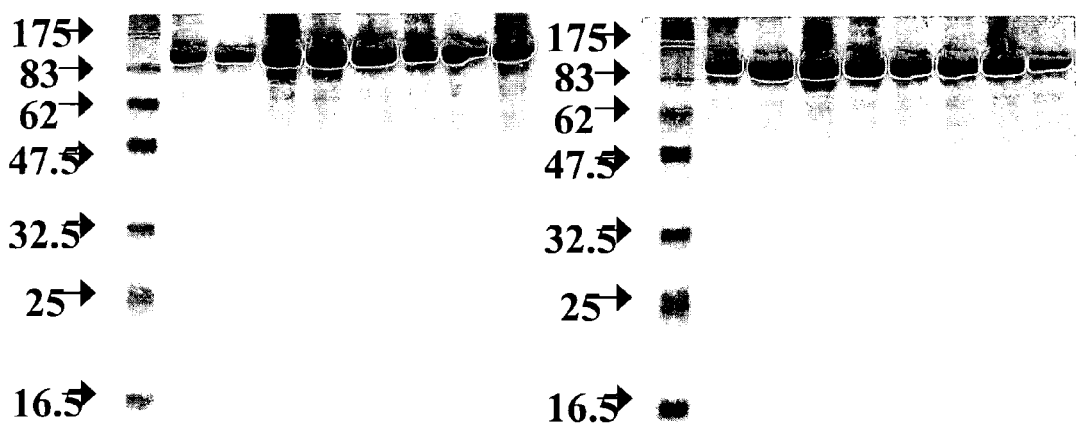
FIG. 2 represents the purification of PTD-β-galactosidase (β-gal) fusion protein and CTP-β-galactosidase fusion protein. M is a prestain marker (NEB), lanes 1–16 represent PTD-β-galactosidase (β-gal), β-gal, CTP50-β-gal, CTP501-β-gal, CTP502-β-gal, CTP503-β-gal, CTP504-β-gal, CTP505-β-gal, CTP506-β-gal, CTP507-β-gal, CTP508-β-gal, CTP509-β-gal, CTP510-β-gal, CTP511-β-gal, CTP512-β-gal and MTS-β-gal, respectively.

Although various other substitutions could be performed, it is essential in this invention that the introduction of a positive charge by arginine and the substitution by an α-helix stabilizing amino acid should be carried out for maintaining the principle function of the PTD peptide. Therefore, as a substitute amino acid, the positively charged amino acid is restricted to arginine, and the negatively charged amino acid is restricted to glutamic acid. β-galactosidase was fused to the CTP candidate peptide, the fusion proteins were isolated and purified (see FIG. 2), and HeLa cells were treated with each of the fusion proteins. This was then followed by an analysis of the transduction potential and a determination of the extent of the cytoplasmic remaining property.

As a result, it was observed that where glycine with a small and flexible structure was introduced into the site of amino acid 2, the function of CTP was significantly increased. While the substitution of amino acid 4, Ala, with the negatively charged Glu resulted in a reduced function of CTP, the increase of the overall content of the positive charge through replacing amino acids 4 and 8 with Arg, was responsible for the increased CTP function.

On the other hand, MTS is a transduction molecule similar to the CTP of this invention, but it is localized in the endoplasmic reticulum rather than the cytoplasm. To compare the transduction potential and cytoplasmic remaining property of MTS to those of CTP, MTS-β-galactosidase fusion protein was purified and underwent experiments.

On the basis of the experimental results described above, novel peptides, CTP 510, 511 and 512 were synthesized and analyzed in terms of their transduction potential and cytoplasmic localization. CTP511 was shown to have a transduction potential and cytoplasmic remaining property similar to PTD, while CTP512 exhibited a higher transduction potential than PTD and an excellent cytoplamic remaining property, so that most of the fusion proteins introduced into the cell were shown to remain in the cytoplasm.

Figure 3:
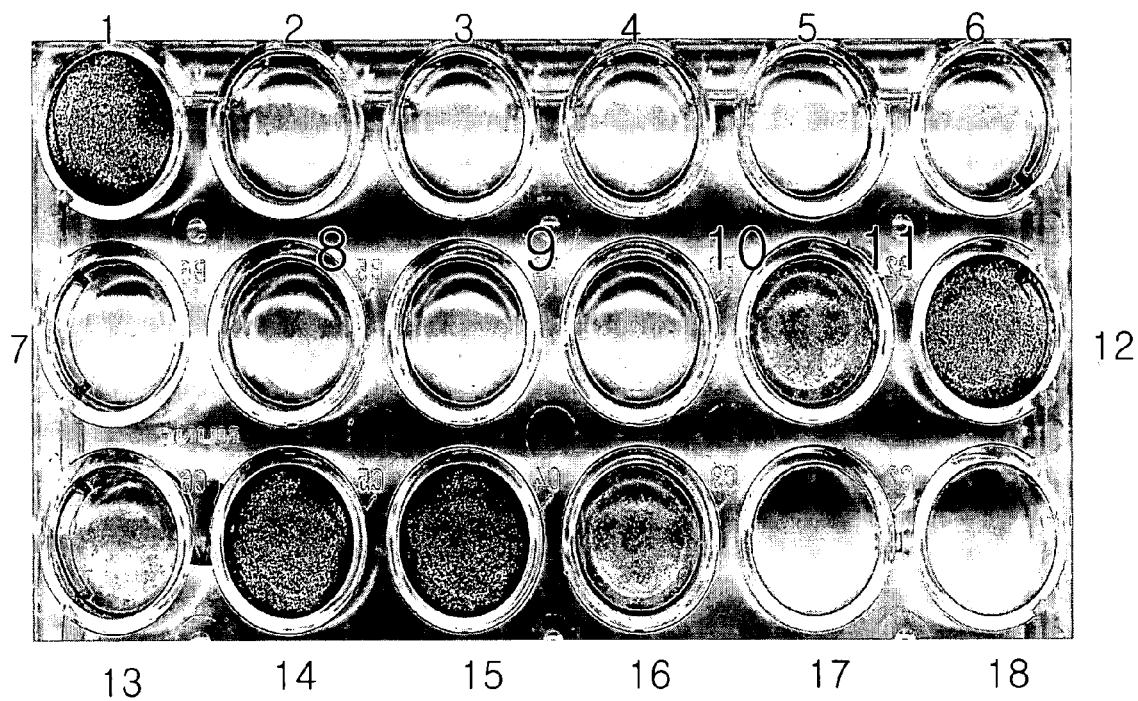
FIG. 3 shows the analysis results of the transduction potential of PTD and CTP (cytoplasmic transduction peptide). Wells 1–16 represent PTD-β-gal, β-gal, CTP50-β-gal, CTP501-β-gal, CTP502-β-gal, CTP503-β-gal, CTP504-β-gal, CTP505-β-gal, CTP506-β-gal, CTP507-β-gal, CTP508-β-gal, CTP509-β-gal, CTP510-β-gal, CTP511-β-gal, CTP512-β-gal and MTS-β-gal, respectively.

In a comparative experiment, MTS fusion protein was shown to have a transduction potential similar to CTP508, which amounts to 20% of the transduction potential of wild type PTD fusion protein (FIG. 3).

A series of cytoplasmic transduction peptides such as CTP512, CTP511, CTP509. and CTP508 that exhibit a significantly high transduction potential and cytoplasmic remaining property, were designed and synthesized.

TABLE 1

| Type | DNA and amino acid sequences | | | | | | | |
|---|---|---|---|---|---|---|---|---|
| Tat (PTD) | tac | ggc | cgc | aag | aaa | cgc | cgc | cag | cgc |
| | cgc | cgc | | | | | | | |
| | Y | G | R | K | K | R | R | Q | R |
| | R | R | | | | | | | |
| CTP50 | tac | gca | cgc | gca | gca | cgc | cgc | gca | gca |
| | cgc | cgc | | | | | | | |
| | Y | A | R | A | A | R | R | A | A |
| | R | R | | | | | | | |
| CTP501 (1P) | cca | gca | cgc | gca | gca | cgc | cgc | gca | gca |
| | cgc | cgc | | | | | | | |
| | P | A | R | A | A | R | R | A | A |
| | R | R | | | | | | | |

TABLE 1-continued

| Type | DNA and amino acid sequences |
|---|---|
| CTP502 (2P) | tac cca cgc gca gca cgc cgc gca gca cgc cgc<br>Y P R A A R R A A R R |
| CTP503 (2R11A) | tac cgc cgc gca gca cgc cgc gca gca cgc gca<br>Y R R A A R R A A R A |
| CTP504 (2G) | tac gga cgc gca gca cgc cgc gca gca cgc cgc<br>Y G R A A R R A A R R |
| CTP505 (4E) | tac gca cgc gaa gca cgc cgc gca gca cgc cgc<br>Y A R E A R R A A R R |
| CTP506 (2E4E) | tac gaa cgc gaa gca cgc cgc gca gca cgc cgc<br>Y E R E A R R A A R R |
| CTP507 (2K) | tac aaa cgc gca gca cgc cgc gca gca cgc cgc<br>Y K R A A R R A A R R |
| CTP508 (4K) | tac gca cgc aaa gca cgc cgc gca gca cgc cgc<br>Y A R K A R R A A R R |
| CTP509 (2K4K) | tac aaa cgc aaa gca cgc cgc gca gca cgc cgc<br>Y K R K A R R A A R R |
| CTP510 (2G4R) | tac gga cgc cgc gca cgc cgc gca gca cgc cgc<br>Y G R R A R R A A R R |
| CTP511 (2G4R8R) | tac gga cgc cgc gca cgc cgc cgc gca cgc cgc<br>Y G R R A R R R A R R |
| CTP512 (2G4R8R9R) | tac gga cgc cgc gca cgc cgc cgc cgc cgc cgc<br>Y G R R A R R R R R R |
| CTP513 (2G4R5R8R9R) | tac gga cgc cgc cgc cgc cgc cgc cgc cgc cgc<br>Y G R R R R R R R R R |
| CTP514 (2R4R5R8R9R) | tac cgc cgc cgc cgc cgc cgc cgc cgc cgc cgc<br>Y R R R R R R R R R R |
| MTS | gca gcc gtt ctt ctc cct gtt ctt ctt gcc gca ccc<br>A A V L L P V L L A A P |

Example 2

Cloning of CTP Candidates in the pTAT-HA LacZ Vector and Protein Purification

Example 2-1

Primer List for CTP Candidates

The pTAT-HA LacZ vector used in this example was kindly provided by Dr. Dowdey at Washington University School of Medicine, in which the LacZ protein is cloned at the XhoI site. The PTAT-HA vector carries a T7 promoter 6× His-tag and Tat domain for the expression and purification of the desired protein, and a multiple cloning site for cloning. For cloning CTP candidates of this invention, pTAT-HA LacZ was digested with BamHI and NcoI to remove the Tat domain and HA-tag region, and then the oligonucleotides encoding CTP candidates of this invention were cloned in pTAT-HA LacZ. The LacZ coding for β-galactosidase protein was cloned at the XhoI region of the pTAT-HA vector.

The amino acid sequences of the CTP candidates are indicated in Table 1. The PTD and CTP candidates consist of 11 amino acids other than MTS (12 amino acids), and the amino acids substituted are indicated in bold letters. The primers for CTP development were purchased from Genotech, Inc (Korea), and each was PAGE-purified. A set of the primers, i.e., forward (f) and reverse (r) primers were synthesized, and were cloned in PTAT-HA LacZ deprived of its Tat domain and its HA domain using the primer annealing method. The nucleotide sequences of the primers synthesized are as follows:

TABLE 2

| Primers | Nucleotide sequences |
|---|---|
| CTP50-f | GAT CCA TGT ACG CAC GCG CAG CAC GCC GCG CAG CAC GCC GCT C |
| CTP50-r | CAT GGA GCG GCG TGC TGC GCG GCG TGC TGC GCG TGC GTA CAT G |
| CTP501-f | GAT CCA TGC CAG CAC GCG CAG CAC GCC GCG CAG CAC GCC GCT C |
| CTP501-r | CAT GGA GCG GCG TGC TGC GCG GCG TGC TGC GCG TGC TGG CAT G |
| CTP502-f | GAT CCA TGT ACC CAC GCG CAG CAC GCC GCG CAG CAC GCC GCT C |
| CTP502-r | CAT GGA GCG GCG TGC TGC GCG GCG TGC TGC GCG TGG GTA CAT G |
| CTP503-f | GAT CCA TGT ACC GCC GCG CAG CAC GCC GCG CAG CAC GCG CAT C |
| CTP503-r | CAT GGA TGC GCG TGC TGC GCG GCG TGC TGC GCG GCG GTA CAT G |
| CTP504-f | GAT CCA TGT ACG GAC GCG CAG CAC GCC GCG CAG CAC GCC GCT C |
| CTP504-r | CAT GGA GCG GCG TGC TGC GCG GCG TGC TGC GCG TCC GTA CAT G |
| CTP505-f | GAT CCA TGT ACG CAC GCG AAG CAC GCC GCG CAG CAC GCC GCT C |
| CTP505-r | CAT GGA GCG GCG TGC TGC GCG GCG TGC TTC GCG TGC GTA CAT G |

TABLE 2-continued

| Primers | Nucleotide sequences |
|---|---|
| CTP506-f | GAT CCA TGT ACG AAC GCG AAG CAC GCC GCG CAG CAC GCC GCT C |
| CTP506-r | CAT GGA GCG GCG TGC TGC GCG GCG TGC TTC GCG TTC GTA CAT G |
| CTP507-f | GAT CCA TGT ACA AAC GCG CAG CAC GCC GCG CAG CAC GCC GCT C |
| CTP507-r | CAT GGA GCG GCG TGC TGC GCG GCG TGC TGC GCG TTT GTA CAT G |
| CTP508-f | GAT CCA TGT ACG CAC GCA AAG CAC GCC GCG CAG CAC GCC GCT C |
| CTP508-r | CAT GGA GCG GCG TGC TGC GCG GCG TGC TTT GCG TGC GTA CAT G |
| CTP509-f | GAT CCA TGT ACA AAC GCA AAG CAC GCC GCG CAG CAC GCC GCT C |
| CTP509-r | CAT GGA GCG GCG TGC TGC GCG GCG TGC TTT GCG TTT GTA CAT G |
| CTP510-f | GAT CCA TGT ACG GAC GCC GCG CAC GCC GCG CAG CAC GCC GCT C |
| CTP510-r | CAT GGA GCG GCG TGC TGC GCG GCG TGC GCG GCG TCC GTA CAT G |
| CTP511-f | GAT CCA TGT ACG GAC GCC GCG CAC GCC GCC GCG CAC GCC GCT C |
| CTP511-r | CAT GGA GCG GCG TGC GCG GCG GCG TGC GCG GCG TCC GTA CAT G |
| CTP512-f | GAT CCA TGT ACG GAC GCC GCG CAC GCC GCC GCC GCC GCT C |
| CTP512-r | CAT GGA GCG GCG GCG GCG GCG GCG TGC GCG GCG TCC GTA CAT G |
| CTP513-f | GAT CCA TGT ACG GAC GCC GCC GCC GCC GCC GCC GCT C |
| CTP513-r | CAT GGA GCG GCG GCG GCG GCG GCG GCG GCG GCG TCC GTA CAT G |
| CTP514-f | GAT CCA TGT ACC GCC GCC GCC GCC GCC GCC GCC GCC GCT C |
| CTP514-r | CAT GGA GCG GCG GCG GCG GCG GCG GCG GCG GCG GTA CAT G |
| MTS-f | GAT CCA TGG CAG CCG TTC TTC TCC CTG TTC TTC TTG CCG CAC CCT C |
| MTS-r | CAT GGA GGG TGC GGC AAG AAG AAC AGG GAG AAG AAC GGC TGC CAT G |

Example 2-2

Cloning CTP Candidates in the PTAT-HA LacZ Vector pTAT-HA LacZ was digested with BamHI and NcoI to remove the Tat domain and the HA-tag domain. The complementary forward and reverse primers for CTP candidates was heated for 5 min at 95° C. and cooled to room temperature at a rate of 1° C./min. The insert sequences were constructed by the primer annealing method mentioned above, and the vectors were ligated (T4 DNA ligase, Roche) for 18 hr at 16° C. to construct a recombinant plasmid. *E. coli* JM109 (Stratagene) was transformed with the recombinant plasmid, cultured in a LB-Amp (50 µg/ml) medium for 18 hr and some of colonies formed were proliferated in LB-Amp medium to obtain recombinant plasmid DNA. The introduction of the CTP candidates was verified by digestion of clones using restriction enzymes. Finally, the analysis of the nucleotide sequences for CTP candidates inserted into recombinant plasmid was performed at SolGent Inc. The nucleotide sequences analyzed were completely consistent with the nucleotide sequences of the primers synthesized above.

Example 2-3

Expression and Purification of PTD and CTP β-gal

*E. coli* BL21 (DE3) (Novagen) was transformed with PTD or CTP-LacZ recombinant plasmids carrying PTD or CTP candidates constructed in Example 2-2, and used in the expression and purification of PTD and CTP-β-galactosidase. The transformed *E. coli* BL21(DE3)/PTD-LacZ or BL21(DE3)/CTP-LacZ transformed was cultured for 18 hr in 250 ml of LB-Amp medium. pTAT-HA LacZ expression plasmid expresses a large amount of the desired gene in the presence of minute quantities of lactose in a LB medium. Therefore, *E. coli* BL21(DE3)/PTD-LacZ or BL21(DE3)/CTP-LacZ was cultured overnight in the absence of IPTG induction.

The transformants cultured in the LB medium were harvested and suspended in 25 ml of lysis buffer (50 mM Na.Pi (pH 7.4), 300 mM NaCl), followed by incubation on ice for 30 min with lysozyme (1 mg/ml). Transformants were sonicated three times for 5 min (40% duty, 6 outputs) to disrupt the cells, centrifuged at 15,000 rpm for 30 min, and the soluble aliquots was loaded on a Ni-NTA resin (Qiagen). The soluble aliquot was equilibrated with a lysis buffer and repeatedly loaded three times on 5 ml of Ni-NTA resin, followed by washing with 25 ml of a lysis buffer containing 20 mM imidazole. The elution was carried out by use of 12 ml of the lysis buffer containing 250 mM imidazole and then analyzed on SDS-PAGE (see FIG. 2).

Through SDS-PAGE analysis, it was verified that 120 kDa PTD and CTP β-gal proteins were purified. The proteins purified were dialyzed in PBS and quantified with Commassie™ Plus-200 Protein Assay Reagent of Pierce Inc. For evaluating protein activity, 40 µl of the substrate solution of 15 mM ONPG (O-nitrophenyl β-D-galactopyranoside) were dissolved in 0.1 M Na.Pi (pH 7.4) buffer, and 80 µl of diluted protein samples with the same amount were added and incubated for 5 min at a room temperature. The reaction was terminated by adding 80 µl of 0.5 M $Na_2CO_3$ and the absorbance at 405 nm was measured with ELISA microplate reader (Bio-Rad) to verify the same activity of protein samples purified.

Example 3

Transduction of PTD and CTP-β-galactosidase into HeLa Cells

The transduction potential of the PTD and CTP candidates was tested with HeLa cells. Using a 24-well plate (Nunc), $5 \times 10^4$ HeLa cells were inoculated into high glucose DMEM (containing 10% FBS) and cultured for 36 hr. The cells were rinsed with PBS and treated with 100 µg/ml of PTD- and CTP-β-galactosidase in an opti-MEM I medium. After 1-hr incubation, cells were fixed for 10 min at room temperature with a fixation solution (2% formaldehyde, 0.2% glutaraldehyde in PBS). Then, the cells were rinsed twice with PBS, and stained for 2 hr with dye (0.1% X-gal, 5 mM potassium ferricyanide, 5 mM potassium ferrocyanide, 2 mM MgCl$_2$ in PBS) to examine their transduction potential (see FIG. 3). The samples showing a low level of staining, even after a 2-hr staining, were incubated overnight, and then stained for the relative transduction potential. The transduction potentials of the PTD and CTP candidates into HeLa cells were seen to be in the following order:

PTD5<CTP502<<CTP501=CTP506<CTP507<CTP505<
CTP503=CTP504<CTP508=CTP510=MTS<CTP509<<
PTD=CTP511<<CTP512.

A comparison of the structural characteristics of low-potential CTP501, CTP502, CTP506 and CTP507 revealed that they have proline (501, 502) at the site of amino acid 2 or 3 where the α-helix starts, a negatively charged amino acid (506) or a positively charged amino acid of a relatively large size (507) at amino acid 2. The difference between PTD5 and CTP504 lies only in an amino acid at the position of amino acid 2. CTP504 has, at this position, a glycine residue with a small and free structure, instead of alanine. Strikingly, CTP504 was found to show a 20-fold higher transduction potential than PTD5 and a high cytoplasmic remaining property. However, this transduction potential of CTP504 corresponds to 10% of that of wild type PTD. These results demonstrate that a glycine residue with a small and flexible structure occupying position 2 of a CTP is pivotal in increasing the desired function of the CTP.

When the structural characteristics of CTP503, CTP504, CTP505, CTP507, CTP508 and CTP509 exhibiting excellent transduction potential were analyzed, it was commonly found that the overall positive charge become higher, irrespective of the amino acid with a large-sized side chain at position 2. In particular, a comparison of CTP508 (2A 4K) and CTP509 (2K 4K) revealed that since CTP509 has an overall positive charge higher than CTP508, it exhibited a transduction potential higher than CTP508, although it had lysine at position 2. In addition, both CTP508 and CTP509 showed a much stronger cytoplasmic remaining property than PTD.

On the basis of the results described previously, to prepare a CTP which shows excellent functions of interest, an amino acid residue at position 2 was substituted with glycine, and amino acid residues at positions 5, 8 and 9 were consecutively substituted with arginine residues to increase the overall positive charge, thereby designing and synthesizing novel CTP 510, 511 and 512. Their transduction potentials and cytoplasmic remaining properties were analyzed.

CTP 511 was found to show a transduction potential identical to PTD and an excellent cytoplasmic remaining property. CTP 512 was observed to exhibit a transduction potential higher than wild type PTD and an excellent cytoplasmic remaining property. Thus the CTP-fused proteins transduced into the cell remained completely in the cytoplasm.

Consequently, the novel peptides, CTPs, exhibiting transduction potential as well as cytoplasmic remaining property, were successfully designed and synthesized.

Example 4

Observations on the Subcellular Localization of CTP-β-gal by a Confocal Scanning Microscope To select cytoplamic transduction peptides (CTPs) of interest, HeLa cells were transduced with CTP-β-galactosidase, and then examined under the confocal scanning microscope. Before the confocal analysis, cells were stained with mouse anti-β-galactosidase antibody and 2$^{nd}$ antibodies conjugated with FITC (Fluorescence-iso-thio-cyanate) or with PE (phycoerythrin) together with DNA staining reagent (green fluorescence SYTO-16 DNA staining dye, Molecular Probe). First, HeLa cells (5×10$^5$ cells/ml) were plated onto a 6-well plate containing sterilized cover-slips and cultured overnight at 37° C. CO2 incubator. The cells were washed with PBS (pH 7.4) and 1 ml of an OPTI-MEM I medium was added, followed by treatment with candidate CTP-fused proteins (100 µg/ml). As a positive control, PTD-β-galactosidase fusion protein was employed, and as a negative control, only β-galactosidase protein was used. Following the treatment with candidate CTP-β-galactosidase fusion proteins, cells were incubated for 1 hr at 37° C. incubator. The cells were rinsed three times with PBS and fixed with 2% paraformaldehyde for 20 min at 4° C. HeLa cells fixed were washed twice with washing buffer (PBS containing 0.2% BSA and 0.02% sodium azide). To stain the cells with antibody, cells were pre-treated with 0.5% Triton X-100 (in PBS, Sigma) at 4° C. for 20 min. Cells were washed three times with washing buffer and then stained with mouse anti-β-galactosidase antibody (diluted 1:2,000, Sigma) for 1 hr at 4° C. as a primary antibody and then washed three times with washing buffer. Cells were then incubated with FITC-conjugated goat anti-mouse IgG (diluted 1:2,000, Jackson Laboratory) as a secondary antibody for 20 min at 4° C. Washed 3 times with the same washing buffer, cells were fixed on a slide glass with fluorescence mounting medium (DAKO) and the edge of slide glass was sealed with nail vanish.

Double staining was carried out with SYTO-16 DNA staining dye as follows: First, the cells were incubated with the primary antibodies under the same conditions and rinsed three times. Then, the cells were incubated at 4° C. for 20 min with PE-conjugated goat anti-mouse IgG PE (diluted 1:2,000, Jackson Laboratory). Washed three times with washing buffer, cells were incubated with SYTO-16 DNA staining dye (diluted 1:1,000, DAKO) for 20 min at 4° C. Cells were fixed and sealed on a slide glass and then examined under a confocal laser scanning microscope.

In the present experiment, LEICA TCS NT SP confocal microscope (LEICA Lasertech GmbH, Heidelverg, Germany) was employed, which was equipped with lager generator of argon (Ar) and krypton (Kr), scanning device, and filter capable of detecting FITC (510–550 nm) and PE (600–660) at independent channel. Photographs were taken by PL-APO X100 objective. For single staining, the cells were sectioned into 4-layers and fluorescence and transmission photographs were taken. For double staining, FITC, PE, and transmission photographs were taken using optimal respective filter.

It has been known in the art that proteins having the NLS enter into nucleus, and most of them are localized in the perinuclear area (Lin et al., 1995). To confirm the subcellular localization of PTD/CTP-β-gal fusion protein, the confocal microscopic observation was performed. PTD fusion proteins mostly transduced to the nucleus since they have an NLS, whereas the CTPs of this invention were localized in the cytoplasm without getting into nucleus (see FIGS. 5a and 5b).

Figure 4A:
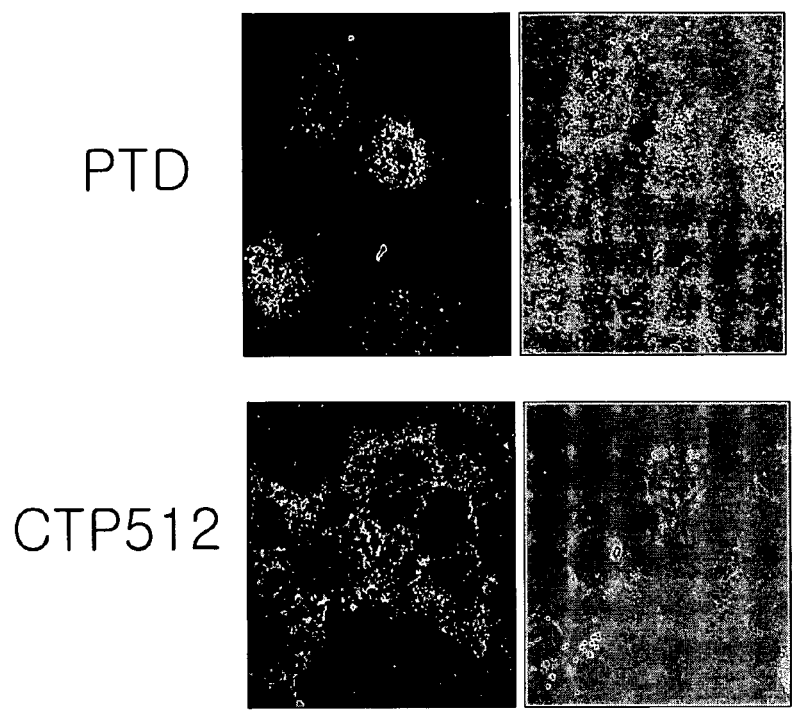
FIG. 4a shows the subcellular localization of the PTD and CTP512 of this invention.
Figure 4B:
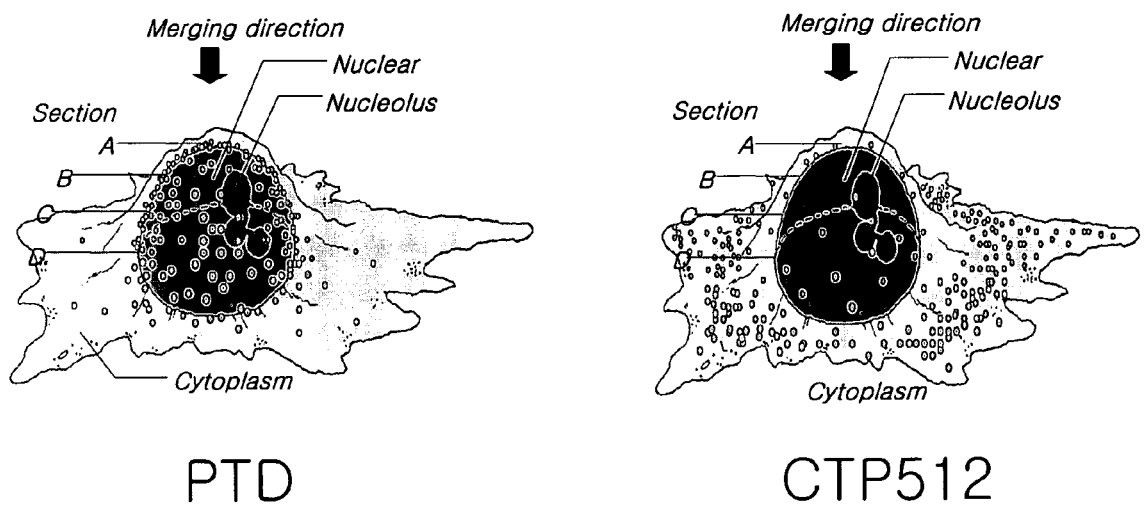

In confocal microscopy, cells are multi-sectioned in three-dimensions and photographed. Overlapping photographs obtained from each section enabled us to examine the three dimensional distribution of proteins. The localization of nucleus in a cell can be revealed by comparison of images obtained from phase contrast microscope. In FIGS. 4a and 4b, the PTD fusion proteins were mostly observed in the nucleus, particularly in the perinuclear area. In contrast, the CTP512 fusion protein showed higher transduction potential than the wild type PTD fusion protein and was mostly localized in the cytoplasm.

Figure 5B:
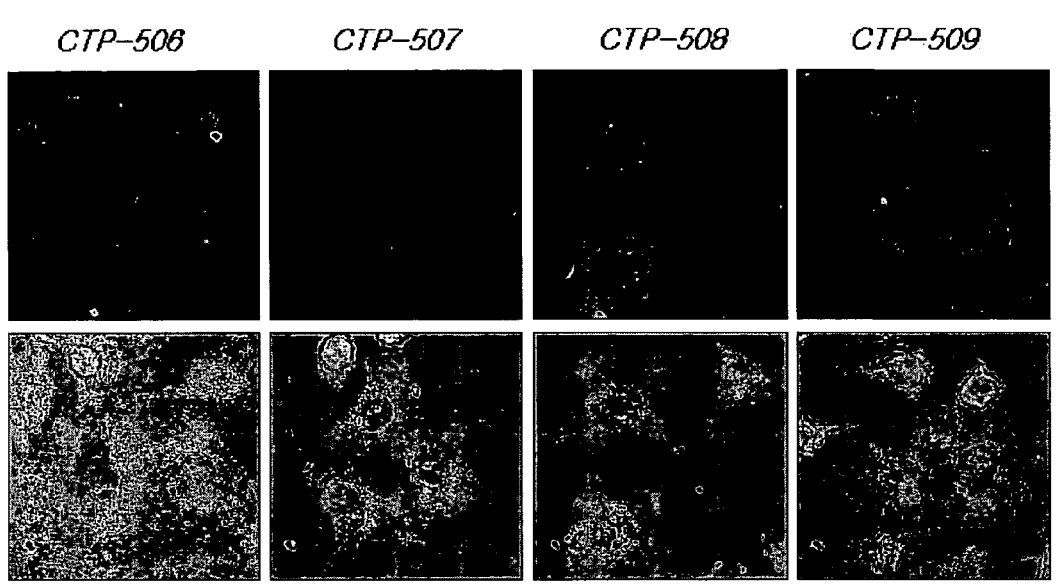
FIG. 5b shows the subcellular localization of the PTD and CTP candidates of this invention.
Figure 5B:
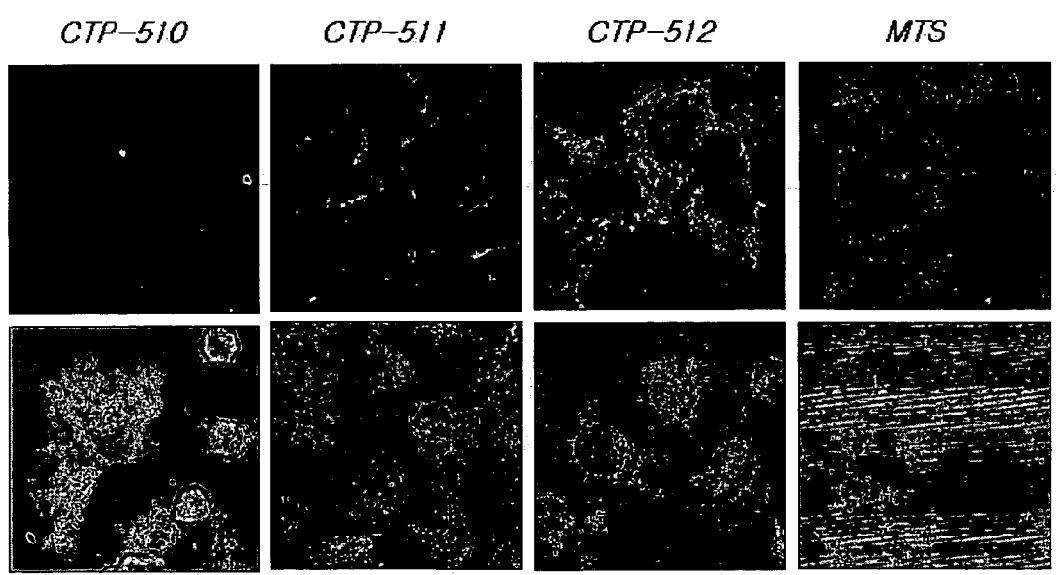

FIG. 5 represents overlapping images of 4 consecutive sections obtained from confocal microscopy. FIG. 3 demonstrates the transduction potential in X-gal staining, and FIGS. 5a and 5b demonstrate the subcellular localization. Taken together of these results, it can be concluded that the novel transduction peptide, CTP512 in the present invention, has a higher transduction potential than the wild type PTD, as well as an excellent cytoplamic localization property. CTP511 showed a transduction potential similar to the wild type PTD, but whose cytoplamic remaining tendency was similar to that of CTP512. Although CTP508 and CTP509 showed transduction potential lower than wild type PTD, their cytoplasmic remaining potential was much higher than the wild type PTD.

Example 5

Analysis of the Authenticity of the Transduction Potential of CTP

Recently, the transduction potential of HIV-1 Tat derived PTD has been challenged. According to several publications, it has been suggested that the transduction potential of PTD may not be ascribed to the cell permeability of the PTD peptide per se, but to the affinity of the PTD peptide to the cell membrane via electrostatic interaction between the positive charges carried in PTD and the negative charges of cell membrane, resulting in being imported into the cells during the fixation. Therefore, it has been suggested that the transduction performances of PTD so far observed can be ascribed to artifact effects (43–45). In addition, it has been reported that where PTD peptide-treated cells are incubated with trypsin for a period of time to remove the PTD attached to the cell membrane, the amounts of PTD introduced into cell significantly decrease, and the authentic transduction potential is predominantly depending on the endocytosis rather than its own membrane permeability (46). Consequently, a re-examination of the transduction potential of a variety of membrane permeable peptides reported so far is now inevitable.

In this regard, the present inventors have investigated the authenticity of the transduction potential of CTP.

Example 5-1

Figure 6A:
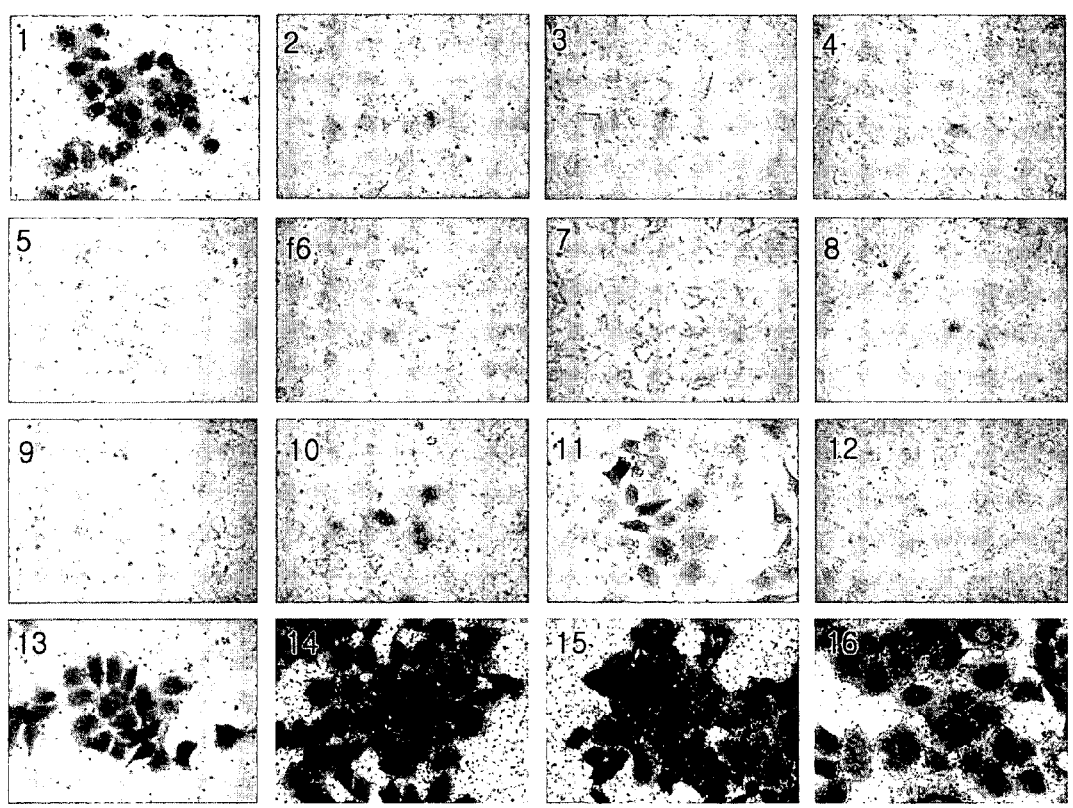
FIG. 6a represents the transduction potential of PTD-β-gal, MTS-β-gal and CTP-β-gal.

Analysis of the Transduction Potential of CTP-β-gal Fusion Protein Without Treatment with Trypsin To compare the transduction potential of cell pentrating peptides (CPP) such as CTP, PTD and MTS, CPP fused β-gal fusion proteines were incubated, respectively, with HeLa cells at a final concentration of 50 μg/ml and enzymatic activity of β-gal introduced into cells was measured. The β-gal activity was measured as described in Example 3, and the stained cells were photographed under a microscope (FIG. 6a). As shown in FIG. 6a, cells treated with CTP512-β-gal showed a β-gal activity much higher than those treated with PTD or MTS. In addition, cells treated with CTP513-β-gal showed a β-gal activity similar to those treated with CTP512-β-gal and cells treated with CTP514-β-gal showed a β-gal activity similar to those treated with PTD-β-gal. However, these experiments could not verify whether the observed β-gal activity is due to the authentic transduction potential of the CPP or was an artifact of cell fixation.

Example 5-2

Analysis of the Transduction Potential of CTP-β-gal following Treatment with Trypsin This analysis was initiated to confirm whether the CTP of this invention is introduced into cells through its authentic transduction potential or through the influence of cell fixation.

HeLa cells were cultured for 1 day in DMEM (high glucose) at a density of $2 \times 10^5$/ml in 48-well plates. Cells were washed once with 1× PBS, and then incubated further for additional 20 hr in OPTI-MEM containing PTD-β-gal, MTS-β-gal, CTP501-β-gal or CTP514-β-gal, respectively, at a concentration of 50 μg/ml. Thereafter, the cells were treated with trypsin-EDTA (10×) for 3 min at 37° C. to remove the CPP-β-gal attached to the cell surface, and then rinsed twice with 1× PBS, followed by fixing with a fixation solution for 10 min at room temperature. After washing twice with 1× PBS, the cells were stained with a staining solution for 2 hr at 37° C. and photographed under a microscope (FIG. 6b).

Figure 6B:
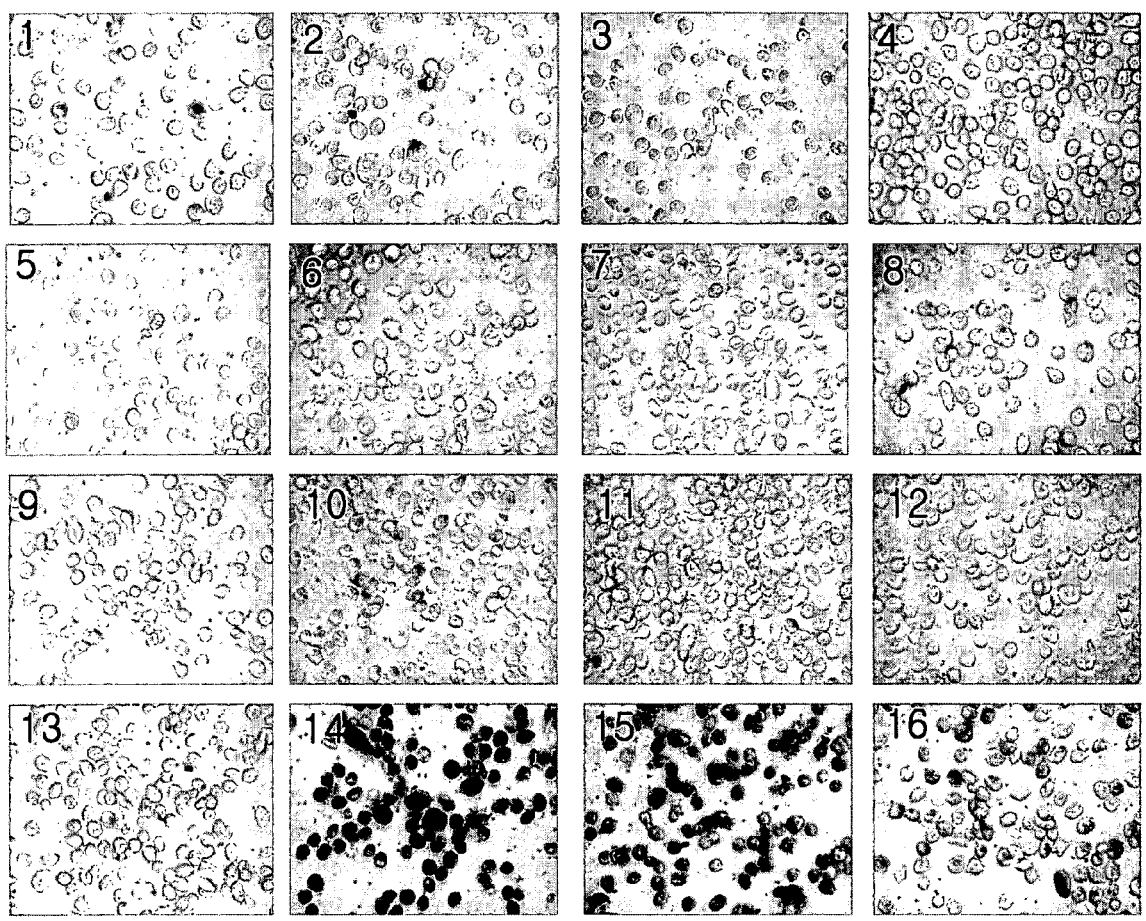
FIG. 6b represents the transduction potential of PTD-β-gal, MTS-β-gal and CTP-β-gal following trypsin treatment prior to cell fixation.

As shown in FIG. 6b, CTP512 or CTP513 was much more efficient to transduce β-gal into cells than either PTD or MTS. The β-gal activity transduced by CTP511 or CTP514 was almost equivalent to that of the PTD. Thus, it is reasoned that at least CTP512 and CTP513 among CTPs of this invention can exhibit a considerably high transduction potential even after trypsinization to exclude artificial transduction of the proteins attached to the cell surface.

Example 5-3

Quantitative Analysis of the Membrane Permeability of CTP-β-gal

For the quantitatation of the permeability of each CPP-fusion protein, HeLa cells were treated with PTD, MTS and CTP508, 509, 511, 512, 513 and 514, CPP-β-gal fusion proteins for 20 hr as described above, and the cells were trypsinized, followed by measuring the amounts of fusion protein imported into cells. Trypsin-treated cells were washed twice with 10% FBS-containing DMEM (high glucose) to inactivate any residual trypsin activity, and then washed once with 1× PBS. The cells collected by centrifugation were resuspended in a 0.9% Triton-X 100 solution, incubated for 10 min at room temperature to lyse cells, and then the supernatant of each lysate was obtained by centrifugation at 12000 rpm for 2 min. The β-gal activity of each sample was measured at 570 nm using enhanced β-gal assay kit (GTS Inc, USA) and an ELISA reader.

Figure 7:
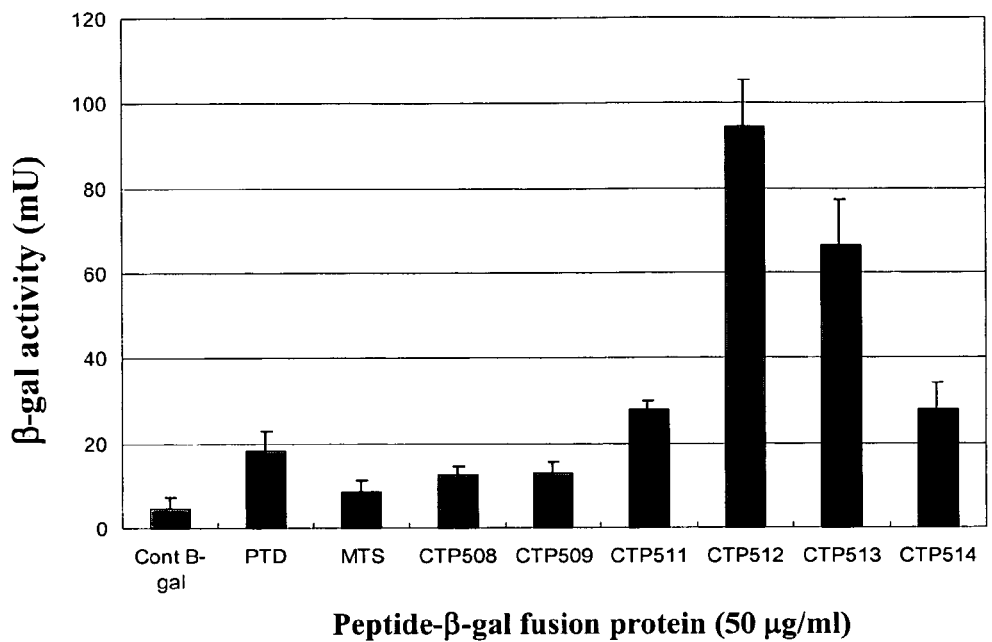
FIG. 7 shows the results of the quantitative analysis on the transduction potential of PTD-β-gal, MTS-β-gal and CTP-β-gal when treated with trypsin prior to cell fixation.

As represented in FIG. 7, the CTP512-β-gal showed a 1.5-fold higher transduction potential than the CTP513 ($Arg_9$)-β-gal. Strikingly, the CTP512-β-gal exhibited about a 4-fold and 7-fold higher transduction potential than the PTD-β-gal or the MTS-β-gal, respectively.

These results clearly demonstrate that the CTP512 has a much higher transduction potential than either the PTD or the MTS even in the forms of fusion proteins. In particular, even after incubation for 20 hr, the PTD-β-gal fusion protein was not so efficient as that of CTP-β-gal for its transduction into HeLa cells. This finding is consistent with the results described in several recent publications (46). In contrast to this, the CTP-β-gal fusion protein was imported efficiently into HeLa cells upto a considerably higher level for 20 hr, although CTP-β-gal fusion protein exhibited little or no transduction potential in the incubation for 1 hr. On the basis of these results, the CTP512 was selected as a representative of the CTPs and was exploited for the following experiments.

Example 5-4

Kinetics on the Transduction of CTP-β-gal and PTD-β-gal

Figure 8:
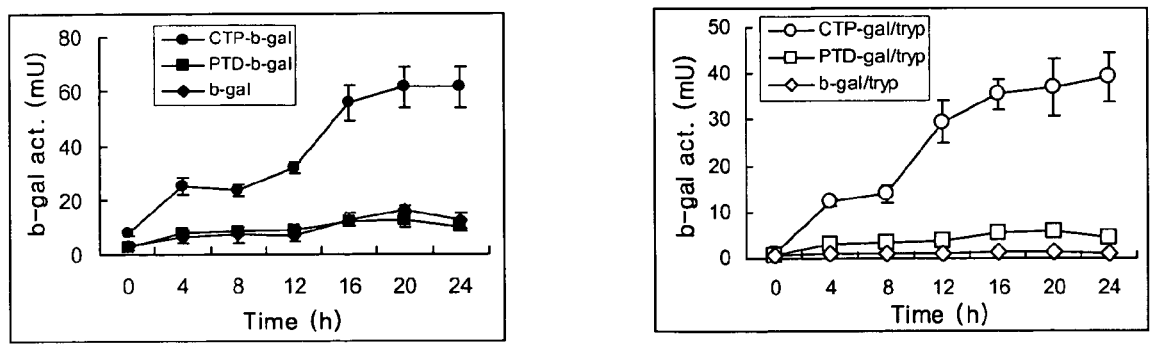
FIG. 8 shows the results of kinetic analysis on the transduction potential of PTD-β-gal and CTP-β-gal.

The Membrane permeability of CTP-β-gal and PTD-β-gal was analyzed in kinetics. Cells were treated with the fusion protein and lysed with 0.9% Triton X-100 solution without trypsinization, after which the overall β-gal activity in the cells was measured. Furthermore, in order to measure the authentic trnsduction amount of β-gal imported into the cells, the cells were trypsinized following the treatment with fusion protein, and then examined the amount of the β-gal activity imported into the cells in the same conditions (see FIG. 8).

When harvested without a trypsinization, the cells showed substantial amounts of the β-gal activity even in a 1 hr treatment of the CTP-β-gal or the PTD-β-gal fusion protein, and the β-gal activity was increased upto 16 hr (see FIG. 8A). It was notable that the cells treated with CTP-β-gal showed significantly higher β-gal activity than those treated with PTD-β-gal for all periods of treatment. In the case where cells were incubated with CTP-β-gal or PTD-β-gal, and then treated with trypsin prior to cell harvest, the β-gal activity in the cells was not detectable in a short period of time, such as 1 hr, since the transport of fusion proteins into cells requires a relatively long period of time (see FIG. 8B). As shown in FIG. 8B, the transport of the fusion protein into cells was increased in the course of time, and the β-gal activity was at its maximum value in about a 20-hr treatment. In this situation, the CTP-β-gal also showed a significantly higher transduction potential than the PTD-β-gal for all periods of treatment The β-gal activity measured without the step of trypsinization was about 2-fold higher than that with the trypsinization step. It means that the half of the β-gal activity in FIG. 8A could be ascribed to cell fixation, rather than to its own transduction potential. Therefore, it becomes evident that the activity of the β-gal imported into cells via transduction cannot be measured accurately if the trypsinization step is exempted prior to harvest the CPP-treated cells. Meanwhile, β-gal protein used as a control was observed not to be imported into cells with the lapse of time.

Considering the results discussed previously, it could be acknowledged that the CTPs of this invention are authentic transduction peptides, exhibiting a noticeable higher transduction potential than PTD.

Example 6

Observation on the Subcellular Localization of CTP-β-gal using a Confocal Microscope According to previous reports, the transduction potential and subcellular localization of PTD is dependent on the type of fusion proteins imported during cell fixation (46). To overcome the shortcomings described above, HeLa cells were treated for 20 hr with 100 μg/ml of the CTP-β-gal and in turn were treated three times with trypsin for 10 sec to remove the CTP-β-gal attached to the cell surface. After that the cells were fixed and examined under confocal microscope to see the subcellular localization of the β-gal. The sample preparation and observation with a confocal microscope was carried out in the same manner as described in Example 4.

Figure 9:
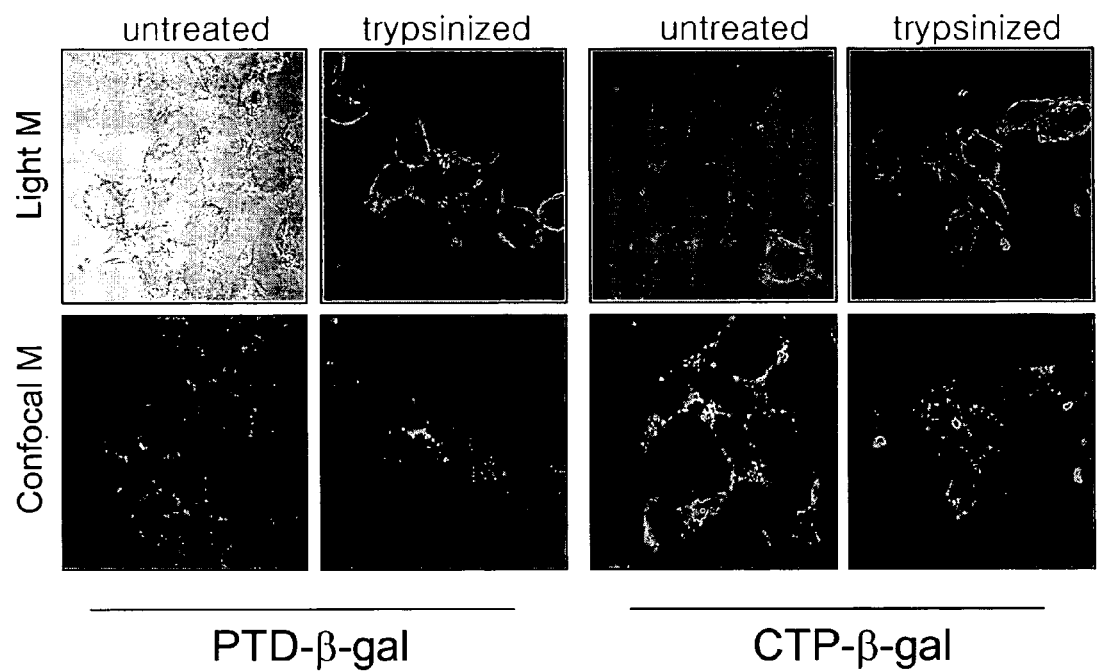
FIG. 9 shows the subcellular localization of PTD-β-gal and CTP-β-gal, as observed under a confocal microscope.

As shown in FIG. 9, the CTP-β-gal was observed to remain in the cytoplasm but not to enter into the nucleus when the CTP-β-gal-treated cells were fixed and examined without trypsinization. In addition, these phenomena of the subcellular localization of the CTP-β-gal was unchanged even when the the CTP-β-gal-treated cells were trypsinized prior to fixation and examination while the amount of the transduced CTP-β-gal in the cytoplasm was slightly decreased and the shape of monolayer and cell morphology were more or less altered. Whereas, the amount of PTD-β-gal introduced into the cells was much smaller than that of CTP-β-gal. Furthermore, the amount of β-gal transduced by PTD disappeared almost when the trypsinization step was included in the confocal examination of the HeLa cells transduced with the PTD-β-gal while substantial amounts of β-gal were detected in the cytoplasm when the trypsinization step was exempted. The results shown in this Example clearly demonstrate that the CTP of this invention is superior to the PTD in view of its transduction potential and it has the unique property of localizing its fusion partner, such as a protein, in cytoplasm.

Example 7

Transduction Potential of CTP512-FITC

It has been shown by trypsin treatment that the transduction potential of the peptides known so far is distorted presumably due to the influence of cell fixation (46). Therefore, to verify that the CTP-β-gal of this invention has genuine transduction potential, trypsinization steps were included in the experiments as described above. At this time, since the activity of CTP per se may be affected by its fusion partner β-gal, CTP labeled with fluorescent molecule instead of β-gal was examined for its transduction capacity into cells. HeLa cells were treated with CTP-FITC and then trypsinized prior to harvest. The amounts of the peptides transduced into the cells were measured by FACS (Fluorescence-activated cell sorter) analysis with FACSCalibur (Becton Dickison, USA).

HeLa cells were inoculated into 12-well plates at a density of $2 \times 10^5$/ml and cultured for 1 day at 37° C. To see whether trypsinization permits the removal of the CTP, the PTD or the MTS attached to the cell surface, 5 μg of the CTP-FITC, PTD-FITC or MTS-FITC peptides (HHMI/Keck Biotechnology Resource Laboratory, Yale University, USA) were treated with trypsin for 3 min at 37° C. and were incubated with cells for 2 hr at a concentration of 2.5 μg/ml. The cells were washed twice and the fluorescent intensity of each sample was measured by FACS.

Figure 10:
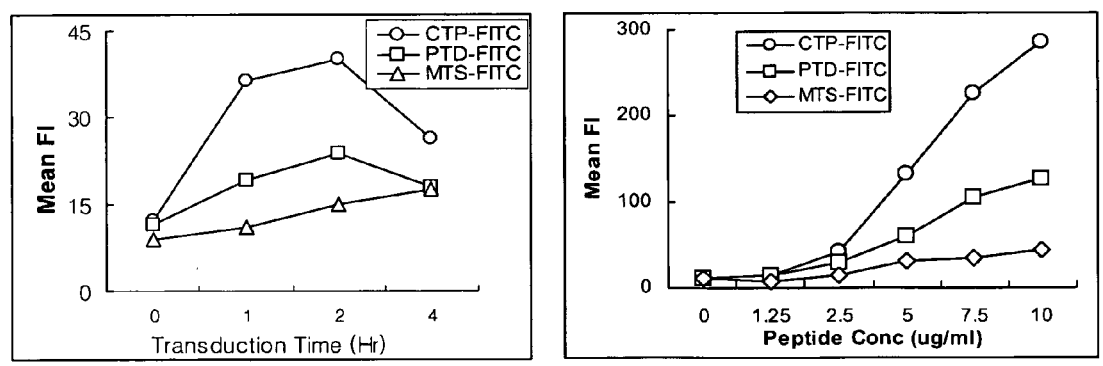
FIG. 10 shows the results of the FACS (Fluorescence-activated cell sorter) analysis demonstrating the transduction potential of PTD-FITC(Fluorescence-iso-thio-cyanate), MTS-FITC and CTP-FITC.

As represented in FIG. 10A, CTP or PTD pretreated with trypsin no longer showed any attachment activity to the cell membrane, suggesting that CTP or PTD peptides attached to the cell surface after transduction could readily be removed by trypsin treatment. However, MTS was shown not to be affected by trypsin, since MTS has no Arg or Lys residue, and therefore is not decomposed by trypsin. In addition, unlike the fusion protein, it was observed that peptides showed their maximum transduction when treated for 2 hr and then a decreased transduction pattern over time. In this situation, the CTP also exhibited a higher transduction potential than the PTD in all period of time. MTS increased for its transduction activity until 8 hr after the treatment, but its transduction potential was much lower than that of CTP or PTD.

In order to examine the transduction potential of peptides at different concentrations, cells were treated for 2 hr with peptides with increasing concentrations of peptides, and then trypsinized before examination. The fluorescent intensity in the cells was measured by FACS. The amounts of peptides introduced into the cells were consecutively increased to 10 µg/ml in dose-dependent manner (FIG. 10B). In addition, it was also observed that at the same concentrations, CTP exhibited a significantly higher transduction potential than either PTD or MTS.

Example 8

Observations on the Subcellular Localization of CTP-FITC using a Confocal Microscope (without Cell Fixation)

Fixation step is inevitable for examining the subcellular localization of the transduced β-gal in the cells with antibodies. However, according to the previous reports, the fusion protein attached to cell surface is very likely to be introduced into the cell during a cell fixation procedure, which may affect its transduction potential and its subcellular localization. However, FITC-labeled membrane permeation peptides allow its subcellular localization to be observed under a confocal microscope without cell fixation. Monolayered HeLa cells were treated for 1 hr with FITC-labeled CTP, PTD or MTS at a concentration of 25 µg/ml, and washed three times with HBSS, followed by observation under a confocal microscope without cell fixation.

Figure 11:
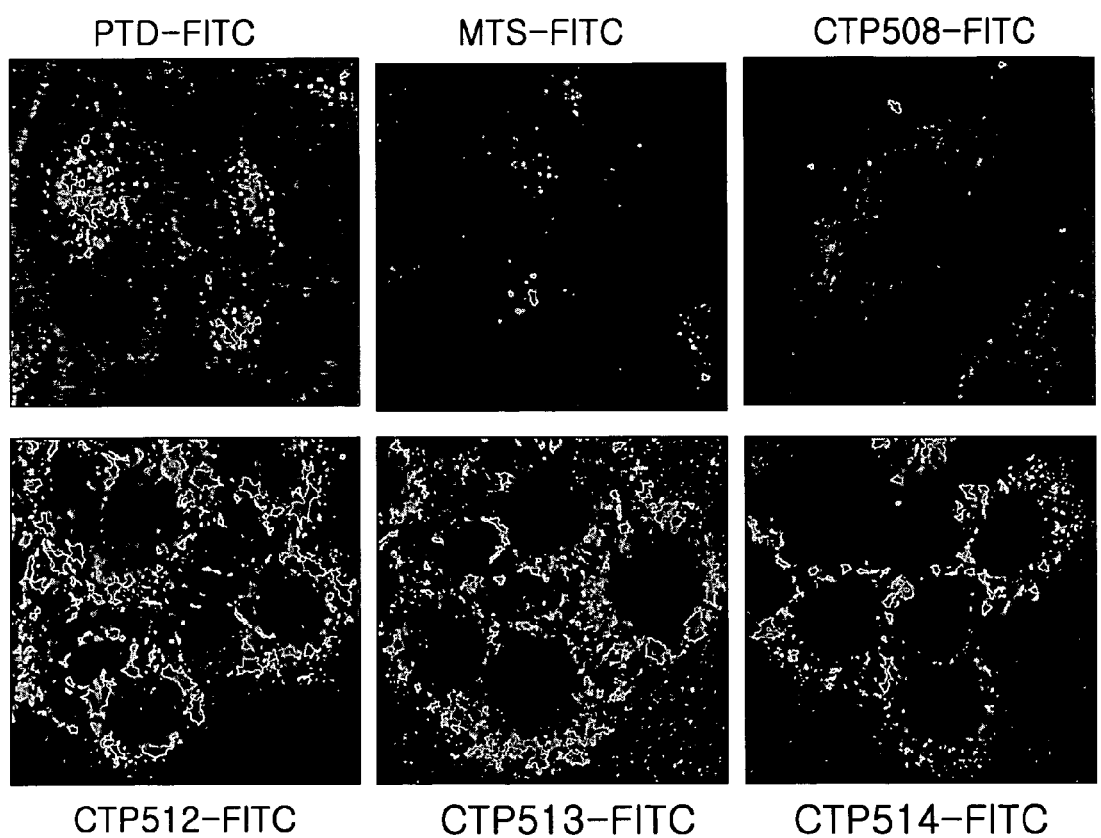
FIG. 11 shows the subcellular localization of PTD-FITC, MTS-FITC and CTP-FITC observed under confocal microscope (without performing cell fixation).

As shown in FIG. 11, CTP 508, 512, 513 and 514 were all observed only in the cytoplasm, and not in the nucleus. The transduction potential was revealed in the following order: CTP512>513>>514>>>508. Such a result is very similar to that of the CTP-β-gal fusion protein. Therefore, it could be deduced that the transduction potential and the subcellular localization of CTP vary, depending on the characteristics of the transduction peptides.

Furthermore, according to these results, cells treated with PTD were observed to exhibit a FITC signal only in the nucleus, but not in the cytoplasm. Therefore, it becomes clear that the PTD transduced into cell has a nuclear localization tendency. In addition, PTD-FITC treated cells showed fluorescence around their surface, suggesting that such a fluorescence signal could be ascribed to peptides attached to cell membrane as shown in FIG. 9. It was expected that such a signal would be extinguished by trypsin treatment. However, trypsinization was not performed to observe the clear subcellular localization of the peptides in the intact shape of the cells.

Example 9

Analysis of Transduction Potential of CTP in Various Cell Type

The examples described above analyzed the transduction potential solely by the use of HeLa cells. In this Example, the transduction potential of CTP was evaluated with other cell types including mouse cell lines (mouse fibroblast L929 and mouse renal cancer cell line RENCA), human lymphoid T cell line (Jurkat cells) and primary mouse splenocytes.

Figure 12:
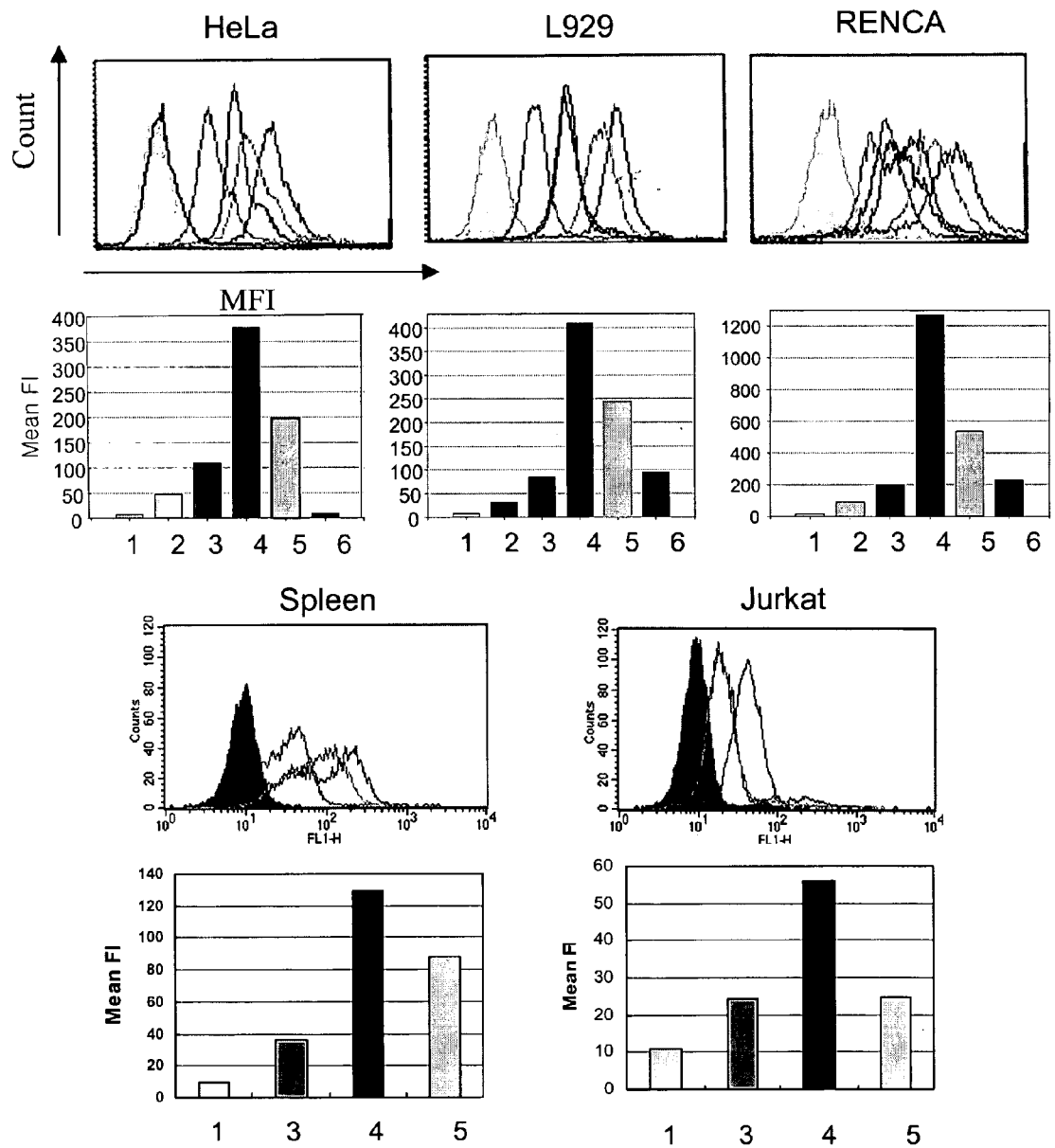
FIG. 12 shows transduction potential of PTD-FITC, MTS-FITC and CTP-FITC in HeLa, L929, RENCA, Jurkat cell lines and splenocytes. Numbers 1–16 under the graphs represent the control, CTP503-FITC, CTP508-FITC, CTP512-FITC, PTD-FITC and MTS-FITC, respectively.

As shown in FIG. 12, the transduction potential of CTPs was slightly or not influenced by the type of cells treated. In all cell types, CTP512 has exhibited the highest transduction potential.

On the basis of these results, it could be concluded that a CTP such as CTP512 can be successfully used as a drug delivery system, irrespective of the cell type. In particular, it is noteworthy that CTPs deprived of their nuclear localization tendency make it possible to avoid damaging the genetic materials in the nucleus, so that a drug using CTP as its delivery system is expected not to exhibit side effects, unlike other conventional transduction peptides. In this regard, the applicability of CTPs as a drug delivery system is excellent.

Example 10

Analysis of the CTP Localization in Vivo

Example 10-1

Migration Analysis of the CTP-β-gal to Liver or Lymph Nodes

To elucidate whether the CTP of this invention can deliver its fusion partner into cells in vivo as well as into cells in vitro, BALB/c mice were injected i.p. with 25 µg/(g of mouse) of CTP-β-gal, PTD-β-gal, MTS-β-gal fusion protein or β-gal protein, or injected i.v. via tail vein with 100 µg/mouse of fusion proteins. Four hr after injection, mice were euthanized and skinned, and their peritoneal cavities were dissected, followed by washing three times with a PBS buffer. After fixation with a fixing solution, whole body was stained in X-gal solution. Each organ was extracted and the β-gal activity was measured.

Figure 13:
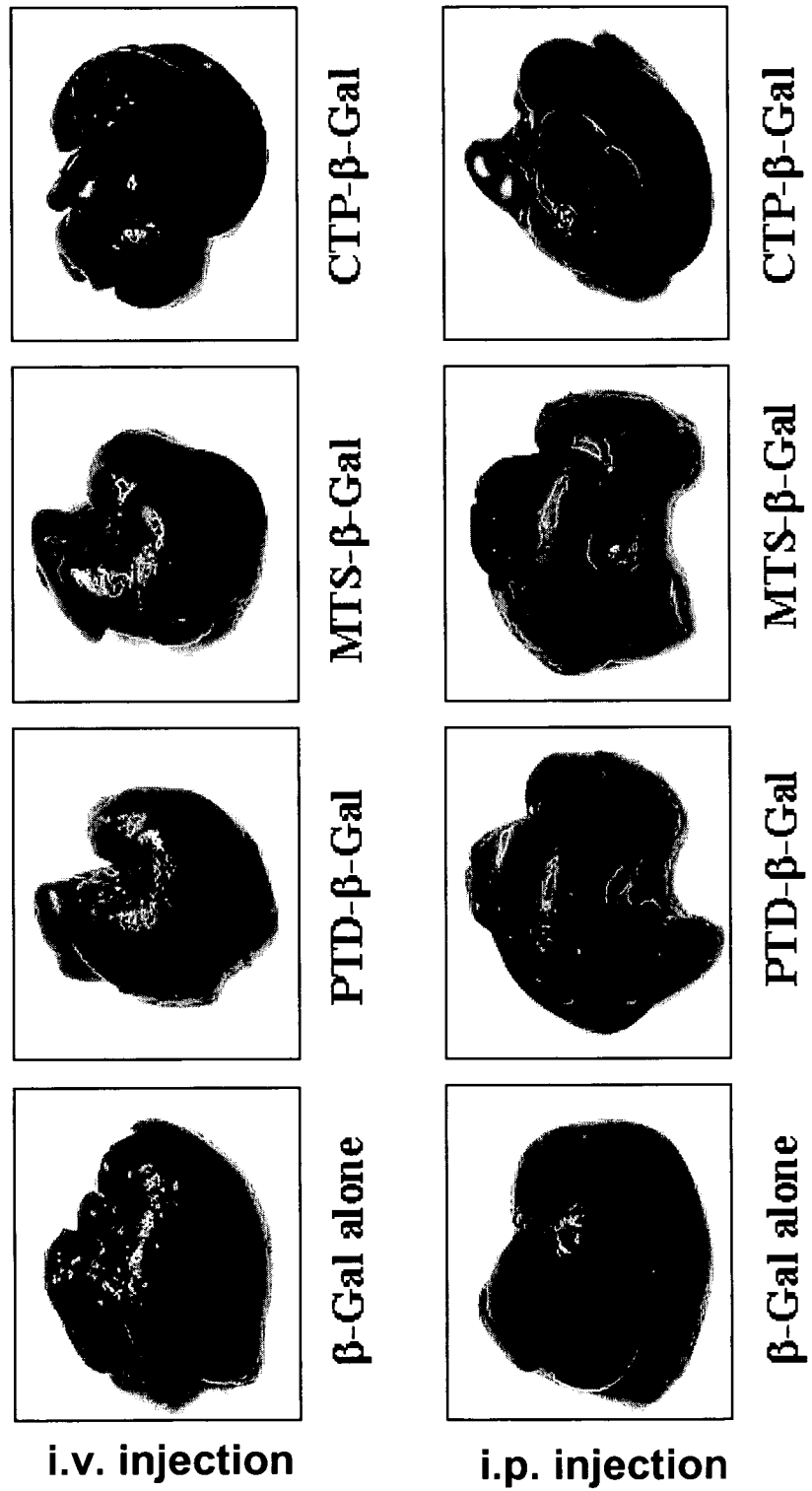
FIG. 13 shows the migration preference of CTP-β-gal to the liver, when administered to mice.

As shown in FIG. 13, in mice injected with CTP-β-gal, the liver showed the highest β-gal activity of all the organs. In addition, those injected i.p. showed a higher β-gal activity than those injected i.v. It is striking that the β-gal activity shown in the liver by the injection of CTP-β-gal was not observed in other mice injected with β-gal, PTD-β-gal or MTS-β-gal.

Figure 14:
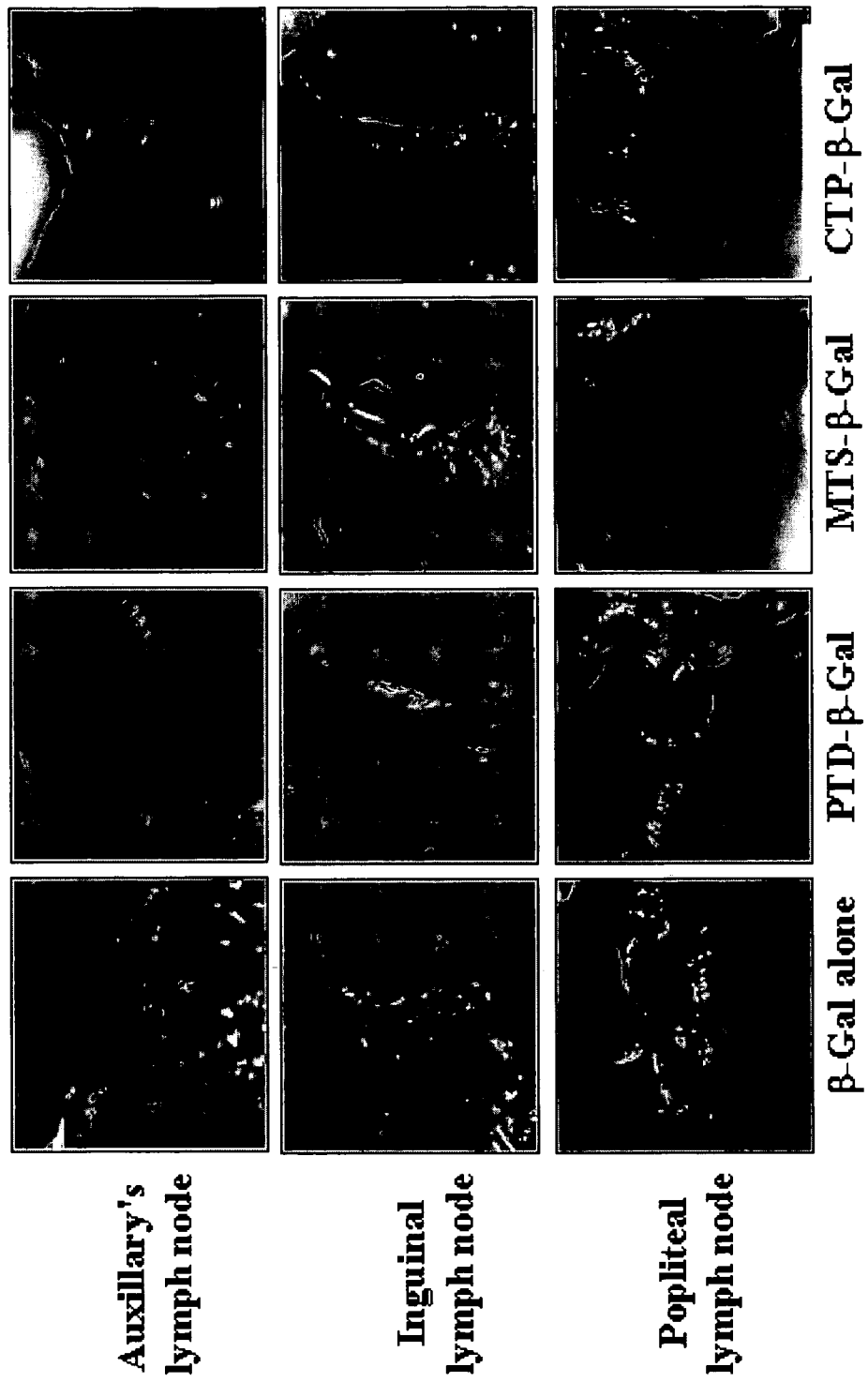
FIG. 14 shows the migration preference of CTP-β-gal to the lymph nodes, when administered to mice.

In mice injected i.v. with CTP-β-gal, the auxiliary lymph nodes, inguinal lymph nodes and popliteal lymph nodes also exhibited a strong β-gal activity; however, β-gal activity was not observed in these organs of the mice injected with PTD-β-gal, MTS-β-gal or β-gal protein, (FIG. 14).

These results demonstrate that CTP has a migration preference in vivo to a particular organ or tissue (liver or lymph node) and that would be considerably useful in a drug delivery system targeting the liver or lymph nodes.

Example 10-2

Analysis of β-gal Activity Infiltrated by CTP in Organ Sections

Figure 15A:
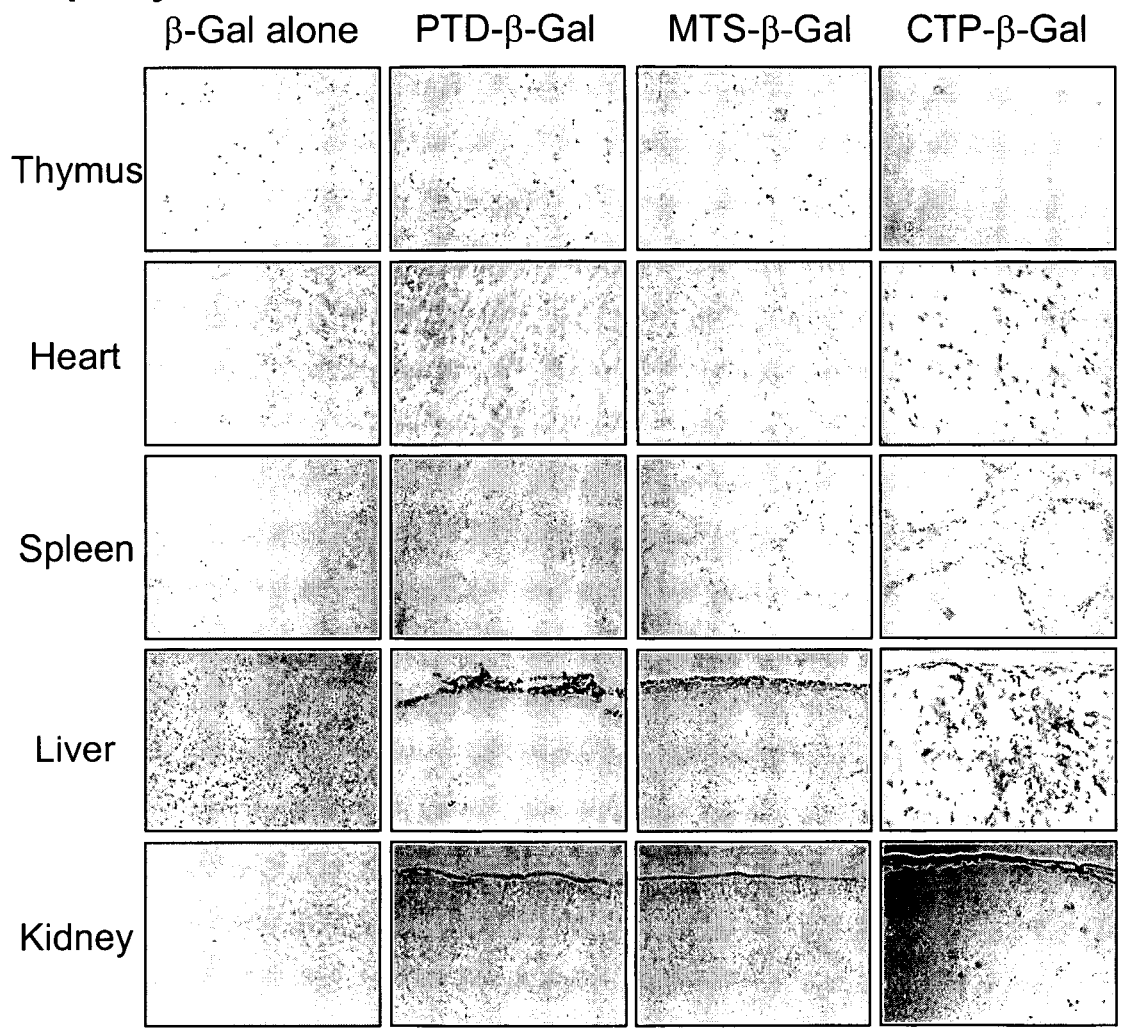
FIG. 15a shows the infiltration of CTP-β-gal into tissues in organs when administered intraperitoneally (i.p.) to mice.
Figure 15B:
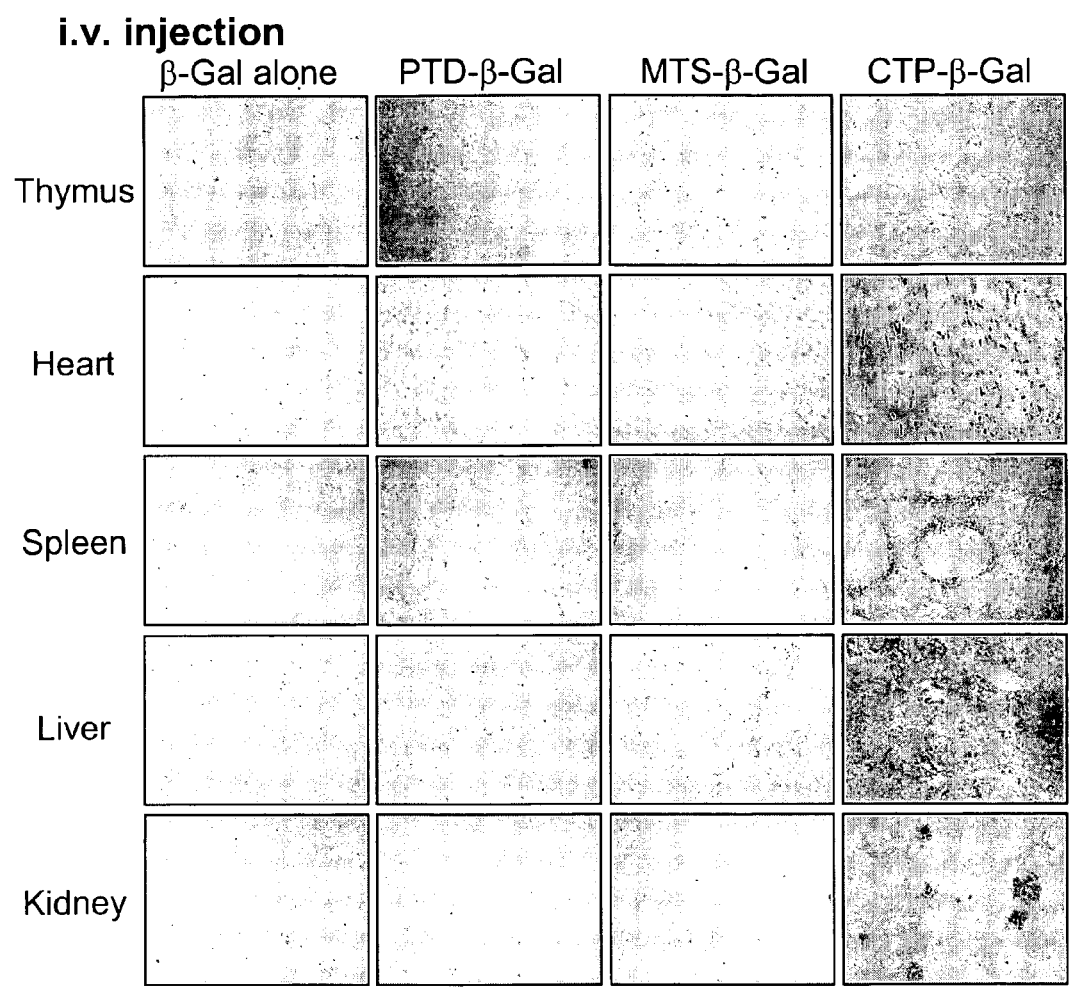
FIG. 15b shows the infiltration of CTP-β-gal into tissues in organs when administered intraveneously (i.v.) to mice.

CTP-β-gal was administered via the peritoneal cavity or a tail vein of mice. Four hr later, organs such as thymus, heart, spleen, liver and kidney were extracted. The organs rapidly frozen were sectioned with a microtome, and then incubated overnight in a X-gal reaction solution, followed by observation of the β-gal activity under a microscope. In CTP-β-gal-administered mice, all parts of the organ sections, except the thymus showed a significant β-gal activity. In contrast, in mice administered with PTD-β-gal, MTS-β-gal or β-gal, the organ sections showed little or no β-gal activity in the inner side. The β-gal activity was only restricted in the outer varrier of the liver or kidney sections in the mice injected with PTD-β-gal and MTS-β-gal (FIGS. 15a and 15b). In CTP-β-gal administration, the β-gal activity observed in the tissue sections was not affected by the administration route, whether it was i.p. (FIG. 15a) or i.v. (FIG. 15b). The β-gal activity shown in the outer varrier of the liver or kidney sections in the mice injected with PTD-β-gal and MTS-β-gal through i.p seemed due to adherence of PTD or MTS to the organ surface. It is noteworthy that other peptides than CTP were unable to infiltrate into the inner part of the memtioned organ.

In this regard, it could be concluded that a drug delivery system comprising CTP could successfully infiltrate into organs, which would therefore enhance drug efficacy.

Example 10-3

Analysis of the Localization of CTP in Organs

Figure 16:
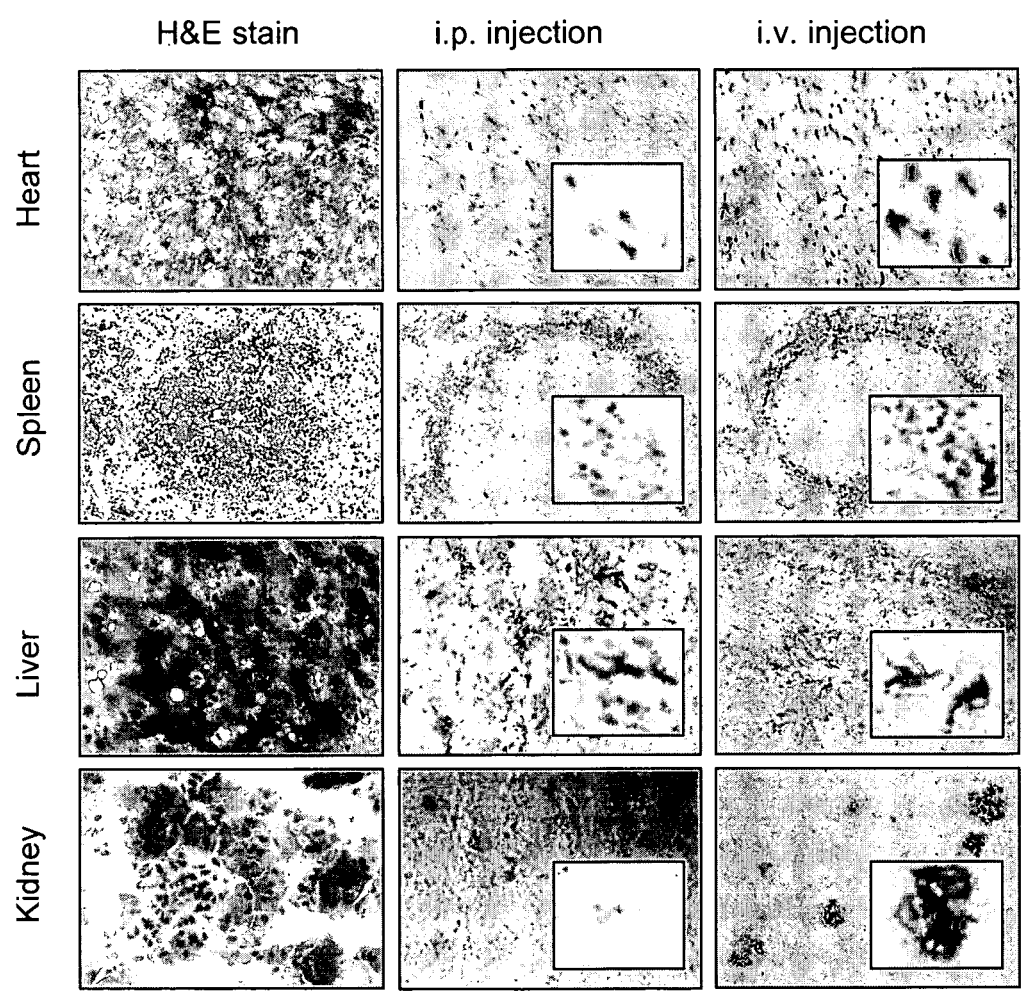
FIG. 16 shows that CTP-β-gal migrated preferentially into a particular region of an organ, when administered i.v. to mice.

FIG. 16 are the photographs showing the magnified images of the X-gal-stained regions of the organs in mice administered i.p. or i.v. with CTP-β-gal. As shown in hematoxylene eosin staining (HE staining), the inner part of each organ maintains its own unique tissue structure, and the β-gal delivered by CTP is localized at a particular region of the tissues, irrespective of their administration route. Therefore, it is presumed that the localization of the CTP-β-gal fusion protein is due to the trnsfer by virtue of a specific cell type as a vehicle to the inner part of the organ, rather than its free migration via blood or other fluids. In particular, in the spleen, i.p. and i.v. administrations showed similar β-gal staining patterns, and it is suggested that such staining occurred at the germinal center of the B cell area and circumstance of the T cell zone, which makes it possible to deduce that the cell transferring the CTP is dendritic cells or macrophages.

Example 11

CTP Application for the Inhibition of Cytoplasmic Functional Protein

XIAP (X-linked inhibitor of apoptosis protein) inhibits apoptosis by binding with a caspase-9 protein which plays an essential role for apoptosis. A zinc-binding BIR domain in XIAP binds to the N-terminal of the caspase-9 small subunit generated in procaspase-9 processing, resulting in the inhibition of the caspase-9-mediated apoptosis. These function of XIAP is hampered by binding with the N-terminal 7-amino acid sequence of the Smac/DIABLO peptide. That is, the Smac/DIABLO peptide serves to facilitate apoptosis. It has been reported that the 7-amino acid sequence of the Smac/DIABLO protein is sufficient to inhibit the XIAP function (47–50).

This Example demonstrates that the CTP-fused 7-amino acid sequence of the Smac/DIABLO peptide facilitates the apoptosis of the cells whose apoptosis has been blocked by transfection of XIAP. Since the first amino acid, alanine, of the 7-amino acid sequence at the N-terminal of the Smac/DIABLO peptide is pivotal in binding to XIAP, as reported previously, CTP was linked to C-terminal of the Smac/DIABLO peptide to prepare Smac/Diablo-CTP-FITC peptide. For detection, FITC was conjugated at the C-terminal of the peptide: Smac/Diablo-CTP-FITC (AVPIAQKSEG-GRRARRRRRK-FITC).

Jurkat E6 ($2 \times 10^5$ cell/ml) were transfected with 10 μg of pcDNA3-XIAP using a transfection reagent, GenePORTER 2 (1 μl/μg DNA) and cultured for 2 days at 37° C. in RPMI containing 10% FBS. Two days later, the cells were washed twice with 1× PBS, and treated with Smac/Diablo-CTP-FITC peptide (synthesized at HHMI, KECK BIOTECH-NOLOGY RESOURCE CENTER) for 2 hr at 37° C. in a serum free media at concentrations of 0.1 μg/ml, 0.5 μg/ml and 1 μg/ml. Then, to measure the extent of apoptosis, the cells were exposed to UV light (40 W) for 50 sec in a culture hood. After 6 hr, the cells were washed twice with 1 × PBS and the apoptozed cells were measured by FACS using Annexin V-FITC apoptosis detection kit (BD Biosciences Pharmingen. Cot: 556547).

Figure 17:
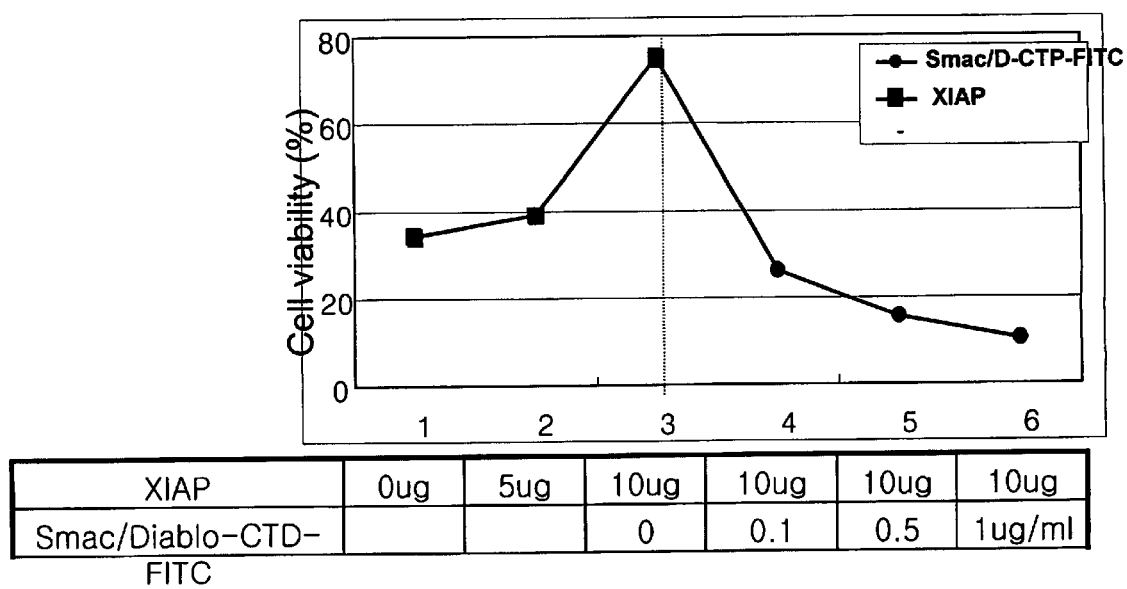
FIG. 17 represents the inhibitory action of the CTP-fusion protein to the function of a cytoplasmic protein, XIAP (X-linked inhibitor of an apoptosis protein).

As shown in FIG. 17, the introduction of an XIAP gene into cells allowed a significant decrease in the extent of the apoptosis induced by UV in proportional to the concentration of the DNA introduced, so that the cell viability was increased. Where cells transfected with 10 μg pcDNA-XIAP DNA were treated with different concentrations of a Smac/Diablo-CTP-FITC peptide, it was observed that apoptosis was greatly increased, even when using 0.1 μg/ml of Smac/Diablo-CTP-FITC.

Consequently, it could be concluded that since the CTP of this invention is excellent in terms of both its transduction potential and cytoplamic remaining property, it is very useful in research and development focusing on cytoplasmic proteins.

The CTP of this invention has a strong tendency to remain in the cytoplasm and not to migrate into the nucleus, and is therefore capable of targeting a specific protein in the cytoplasm without eliciting any side effects associated with genetic material. Therefore, CTP is very useful in developing a drug delivery system designed to remain in cytoplasm.

The present invention provides a cytoplasmic transduction peptide (CTP). The cytoplasmic transduction peptide of this invention shows a transduction potential identical to or higher than that of the conventional transduction domain, PTD, and has a strong tendency to remain in the cytoplasm and not to migrate into the nucleus. Therefore, the CTP of this invention is very useful in delivering a variety of materials into the cytoplasm Throughout this application, various publications and patents are referenced, and citations are provided in parentheses. The disclosures of these publications and patents in their entireties are hereby incorporated as references in this application, in order to more fully describe this invention and the state of the art to which this invention pertains.

Having described a preferred embodiment of the present invention, it is to be understood that variants and modifications thereof falling within the spirit of the invention may become apparent to those skilled in this art, and the scope of this invention is to be determined by the appended claims and their equivalents.

REFERENCES

1. Green, M., et al. 1988. *Cell* 55, 1179–1188.
2. Frankel, A. D., et al. 1988 *Cell* 55, 1189–1193.
3. Vives, E., et al. 1997 *J. Biol. Chem.* 272, 16010–16017.
4. Futaki, S., et al. 2001. *J. Biol. Chem.* 276, 5836–5840.
5. Suzuki, T., et al. 2002. *J. Biol. Chem.* 277, 2437–2443.
6. Hakansson, S., et al. 2001. *Protein Sci.* 10, 2138–2139.
7. Tyagi, M., et al. 2001. *J. Biol. Chem.* 276, 3254–3261.
8. Rusnati, M., et al. 1997. *J. Biol. Chem.* 272, 11313–11320.
9. Wender, P. A., et al. 2000. *Proc. Natl. Acad. Aci. U.S.A.* 97, 13003–13008.
10. Mitchell, D. J., et al. 2000. *J Pept. Res.* 56, 318–325

11. Schwarze, S. R., et al. 1999. *Science* 285, 1569–1572.
12. Kim, D. T., et al. 1997. *J. Immunol.* 159, 1666–1668.
13. Schwarze, S. R., et al. 2000. *Trends Cell Biol.* 10, 290–295.
14. Gius, D. R., et al. 1999. *Cancer Res.* 59, 2577–2580
15. Nagahara, H., et al. 1998. *Nat. Med.* 4, 1449–1452.
16. Mai, J. C., et al. 2001. *Cancer Res.* 61, 7709–7712.
17. Xia, H., et al. 2001. *Nat. Biotechnol.* 19, 640–644.
18. Embury, J., et al. 2001. *Diabetes* 50, 1706–1713.
19. Rothbard, J. B., et al. 2000. *Nat. Med.* 6, 1253–1257.
20. Lewin M, et al. 2000. *Nat. Biotechnol.* 18, 410–414.
21. Vocero-Akbani, A. M., et al. 1999. *Nat. Med.* 5, 29–33.
22. Derossi, D., et al. 1994. *J. Biol. Chem.* 269, 10444–10450.
23. Derossi, D., et al. 1996. *J. Biol. Chem.* 271, 18188–18193.
24. Derossi, D., et al. 1998. *Trends Cell Biol.* 8, 84–87.
25. Joliot, A., et al. 1991. *Proc. Natl. Acad. Aci. U.S.A.* 88, 1864–1868.
26. Elliott, G., & O'Hare, P. 1997. *Cell* 88, 223–233.
27. Loret, E. P., et al. 1991. *Biochemistry* 30, 6013–6023.
28. Gregoire, C. J., & Loret, E. P. 1996. *J. Biol. Chem.* 271, 22641–22646.
29. Mujeeb, A., et al. 1994. *Proc. Natl. Acad. Sci. U.S.A* 91, 8248–8252.
30. Ho, A., et al. 2001. *Cancer Res.* 61, 474–477.
31. Fawell, S., et al. 1994. *Proc. Natl. Acad. Aci. U.S.A.* 91, 664–668.
32. Hawiger J. 1999. *Curr Opin Chem Biol.* 3, 89–94.
33. Hawiger J. 1997. *Curr Opin Immunol.* 9, 189–194.
34. Lin Y Z, et al. 1995. *J Biol Chem.* 270, 14255–14258.
35. Liu K Y, et al. 1996. *Proc Natl Acad Sci USA.* 93, 11819–11824.
36. Rojas M, et al. 1998. *Nat Biotechnol* 16, 370–375.
37. Wang R F, Wang H Y. 2002. *Nature Biotechnol* 20, 149–154.
38. Cokol M, et al. 2000. *EMBO Rep.* 1, 411–415.
39. Bonifaci N, et al. 1997. *Proc Natl Acad Sci USA.* 94, 5055–5060.
40. Tinland B, et al. 1992. *Proc Natl Acad Sci USA.* 89, 7442–7446.
41. Moede T, et al. 1999. *FEBS Lett.* 461, 229–324.
42. Fontes M R, et al. 2000. *J Mol Biol.* 297, 1183–1194.
43. Lundberg, M., Johansson, M. 2001. *Nat. Biotechnol.* 19, 713–714.
44. Lundberg, M., Johansson, M. 2002. *Biochem. Biophys. Res. Commun.* 291, 367–371.
45. Leifert, J. A., et al. 2002. *Gene Therapy* 9, 1422–1428.
46. Richard, J. P., et al. 2003. *J. Biol. Chem.* 278, 585–590.
47. Zhihong L., et al. 2000. *Nature* 408, 1004–1008.
48. Srinivasa M. S., et al. 2001. *Nature* 410, 112–116.
49. Geng Wu., et al. 2001. *Nature* 408, 1008–1012.
50. Donald W. N. 2001. *Nature* 410, 33–34.

---

What is claimed is:

1. A cytoplasmic transduction peptide characterized in that said cytoplasmic transduction peptide has a cell membrane transduction potential; wherein when a cell is treated with said cytoplasmic transduction peptide for a period of time and then treated with a protease, a cell membrane transduction by said cytoplasmic transduction peptide continues to occur; and after said cell membrane transduction, said cytoplasmic transduction peptide remains in the cytoplasm of said cell, wherein said cytoplasmic transduction peptide comprises an amino acid sequence selected from the group consisting of SEQ ID NOs:1, 2 and 13.

2. The cytoplasmic transduction peptide according to claim 1, wherein said cytoplasmic transduction peptide comprises the amino acid sequence of SEQ ID NO:1.

3. A nucleic acid molecule encoding the cytoplasmic transduction peptide according to claim 1.

4. A cytoplasmic transduction system comprising the cytoplasmic transduction peptide according to claim 1 and a biologically active molecule covalently linked to said peptide.

5. A method for delivering a biologically active molecule into a cytoplasm of a cell, which comprises contacting the cytoplasmic transduction system according to claim 4 to said cell.

6. A method for delivering a biologically active molecule into a cytoplasm of cells of an individual, which comprises administering the cytoplasmic transduction system according to claim 4 to said individual.

7. The method according to claim 6, wherein said cell is liver cell or lymphoid cell.

* * * * *